US012377211B1

(12) United States Patent
Auernhammer

(10) Patent No.: US 12,377,211 B1
(45) Date of Patent: Aug. 5, 2025

(54) HOLD ASSISTANCE DEVICE FOR USE WITH A MEDICAMENT DELIVERY DEVICE

(71) Applicant: Genzyme Corporation, Cambridge, MA (US)

(72) Inventor: Markus Daniel Auernhammer, Frankfurt am Main (DE)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/984,900

(22) Filed: Dec. 17, 2024

(51) Int. Cl.
*A61M 5/158* (2006.01)
*A61M 5/32* (2006.01)

(52) U.S. Cl.
CPC .......... *A61M 5/158* (2013.01); *A61M 5/3204* (2013.01); *A61M 2005/1586* (2013.01)

(58) Field of Classification Search
CPC ........ A61M 2005/1586; A61M 5/3204; A61M 5/3202; A61M 2025/09116; A61M 39/286; A61M 2005/3217; A61M 5/3219; A61M 5/3205; A61M 2005/3265; A61M 2005/3267; A61M 5/3271; A61M 5/158
See application file for complete search history.

(56) References Cited

U.S. PATENT DOCUMENTS

2017/0304542 A1* 10/2017 Helmer ............... A61M 5/2466

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

* cited by examiner

*Primary Examiner* — Theodore J Stigell
(74) *Attorney, Agent, or Firm* — Fish & Richardson P.C.

(57) ABSTRACT

A hold assistance device for use with a medicament delivery device including a moveable needle cover. The hold assistance device comprises a housing coupled to a medicament delivery device, the housing comprising a proximal end and a distal end defining an axis between the proximal and distal ends; a holding element coupled to the housing and moveable relative to the housing in a direction substantially normal to the axis of the housing between a disengaged position and an engaged position; wherein the holding element is disposed outwardly from the axis in the disengaged position and is disposed inwardly towards the axis in the engaged position configured in the engaged position such that the holding element can engage with an aperture or recess in a needle cover of a medicament delivery device when the hold assistance device is coupled thereto, to resist movement of the needle cover relative to the housing.

25 Claims, 21 Drawing Sheets

HOLD ASSISTANCE DEVICE FOR USE WITH A MEDICAMENT DELIVERY DEVICE

TECHNICAL FIELD

The present disclosure relates to a hold assistance device for use with a medicament delivery device; to a medicament delivery system comprising a hold assistance device and a medicament delivery device; and to a method of operating a medicament delivery system.

BACKGROUND

Medicament delivery devices can be used to deliver a range of medicaments. In some devices, the device must be held in a holding position at an injection site to ensure that the correct dose of medicament is dispensed from the device, before removing the device from the injection site. It may be difficult to hold the device in the holding position whilst the medicament is dispensed. This may result in pain, discomfort, a wet injection site, early device removal and/or partial delivery of the medicament. Administering an injection involves several risks and challenges, encompassing both mental and physical aspects.

SUMMARY

The present disclosure provides a hold assistance device to assist a user with the holding of a medicament delivery device in the holding position whilst the medicament is dispensed.

The present disclosure provides a hold assistance device for use with a medicament delivery device which comprises a moveable needle cover, the hold assistance device comprising:
  a housing configured to be coupled to a medicament delivery device, the housing comprising a proximal end and a distal end defining an axis between the proximal and distal ends;
  a holding element coupled to the housing and moveable relative to the housing in a direction substantially normal to the axis of the housing between a disengaged position and an engaged position;
  wherein the holding element is disposed relatively further outwardly from the axis in the disengaged position and is disposed relatively further inwardly towards the axis in the engaged position configured in the engaged position such that the holding element can engage with an aperture or recess in a needle cover of a medicament delivery device when the hold assistance device is coupled thereto, to resist movement of the needle cover relative to the housing.

The housing may comprise a passage extending between the proximal and distal ends to receive a medicament delivery device with which the hold assistance device is to be used, the passage defining the axis.

The holding element may comprise a roller. The roller may be rotatable. The holding element may comprise a projection, a protrusion, a boss, a bar, a ball, a block, a sphere or a hemi-spherical projection.

The hold assistance device may comprise a plurality of holding elements. The plurality of holding elements may comprise two holding elements. The holding elements may be disposed on opposite sides of the housing. The housing may comprise cut-outs or recesses to receive the or each holding element in the engaged position.

Where the holding element comprises one or more rollers, at least one of the rollers or each roller may comprise one or more spindle elements disposed at axially opposite ends of the or each roller. The spindle elements may be received in slots to enable the roller to rotate. The spindle elements being received in the slots may enable the or each roller element to move relative to the housing in a direction substantially normal to the axis of the housing between the disengaged and engaged positions.

The spindle elements may be formed integrally with the or each roller. The spindle elements may comprise a spindle bar or rod extending through central axis of the respective roller.

The hold assistance device may comprise one or more holding element biasing members. The or each holding element biasing member may comprise a spring or a resilient deflectable member. The or each holding element biasing member may be configured to bias the or each holding element inwardly relative to the axis of the housing towards the engaged position. When the or each holding element is in the disengaged position, the holding element biasing member or spring may be arranged to be in a compressed state, and when the holding element is in the engaged position, the holding element biasing member or spring may be arranged to be in a less compressed state than when in the disengaged position.

The or each holding element biasing member may alternatively be configured to bias the or each holding element outwardly relative to the axis of the housing towards the disengaged position. When the or each holding element is in the engaged position, the holding element biasing member or spring may be arranged to be in a compressed state, and when the holding element is in the disengaged position, the holding element biasing member or spring may be arranged to be in a less compressed state than when in the engaged position.

The or each holding element may be mounted one or more arms, wherein the or each arm is moveable to allow the holding element to move between the disengaged and engaged positions.

The or each arm may be pivotable about a pivot point. The or each pivot point may be disposed at an opposite end of arm to holding element. The or each arm may be pivotably attached to the housing. The or each holding element biasing member may be configured to act on the respective arm to bias the respective holding element towards the engaged position. Alternatively, the or each holding element biasing member may be configured to act on the respective arm to bias the respective holding element towards the disengaged position.

The or each arm may be resiliently deformable. The or each arm may be in a relaxed position when the respective holding element is in the disengaged position, and may be in a resiliently deformed position when the respective holding element is in the engaged position, such that the respective holding element is biased towards the disengaged position by the elastic deformation of the respective arm. Alternatively, the or each arm may be in a relaxed position when the respective holding element is in the engaged position, and may be in a resiliently deformed position when the respective holding element is in the disengaged position, such that the respective holding element is biased towards the engaged position by the elastic deformation of the respective arm. The or each arm may be arranged inside the housing.

The hold assistance device may further comprise a constraining element coupled to the housing and moveable between an unconstrained position in which the constraining element enables the holding element to remain in the disengaged position, and a constrained position in which the constraining element retains the holding element in the engaged position. The hold assistance device may comprise two or more constraining elements, and/or may comprise at least one constraining element for a respective holding element.

The or each constraining element may be moveable in an axial direction of the housing between the unconstrained position and the constrained position. The or each constraining element may move in distal direction from unconstrained position towards constrained position, and move in the proximal direction from constrained position to unconstrained position.

The or each holding element and the respective constraining element may be configured such that as the respective constraining element is moved from the unconstrained position towards the constrained position, the constraining element contacts the respective holding element and urges the holding element from the disengaged position to the engaged position.

The or each constraining element may comprise a plate slidably mounted to the housing. Alternatively, the constraining element may comprise a collar, arcuate slideable member. The or each constraining element may extend at least partially around the outer perimeter of the housing.

The hold assistance device may comprise a constraining element biasing member configured to bias the constraining element into the unconstrained position. The constraining element biasing member may comprise a spring. The hold assistance device may comprise a plurality of constraining element biasing members, one or more for each constraining element as provided in the hold assistance device.

The or each constraining element may comprise a finger flange protruding outwardly with respect to the axis of the housing to facilitate a user moving the respective constraining element from the unconstrained position to the constrained position.

The housing may comprise first and second housing portions which are moveable from an open position to allow placement of a medicament delivery device within the housing, and a closed position in which the housing is fixedly secured to the medicament delivery device within the housing.

The first and second housing portions may be hingedly connected by a hinge member and pivotable relative to each other to move between the open and closed positions. The first and second housing portions may be configured such that the housing is of a generally clam-shell configuration. The hinge member may be a living hinge formed integrally with the first and second housing portions. The hinge member may be a hinge rod or hinge bar connecting first and second housing portions.

The housing may comprise a locking mechanism configured to secure the first and second housing portions in the closed position. The locking mechanism may comprise a locking catch or arm formed on one of the first and second housing portions. The locking mechanism may comprise a locking recess or notch formed on the other of the first and second housing portions configured to engage with the locking catch or arm. The locking mechanism may comprise a clip other suitable mechanical connection.

The housing may further comprise third and fourth housing portions which are moveable from an open position to allow placement of a medicament delivery device within the housing, and a closed position in which the housing is fixedly secured to the medicament delivery device within the housing. The third and fourth housing portions may thereby enable the hold assistance device to be fixedly secured to a medicament delivery device by placing the third and fourth housing positions in the closed position around the medicament delivery device, before the first and second housing portions are moved from the open position to the closed position.

The third and fourth housing portions may be hingedly connected and pivotable relative to each other to move between the open and closed positions. The third and fourth housing portions may be configured such that the housing is of a generally clam-shell configuration. The hinge member may be a living hinge formed integrally with the third and fourth housing portions. The hinge member may be a hinge rod or hinge bar connecting third and fourth housing portions.

The housing may comprise a locking mechanism configured to secure the third and fourth housing portions in the closed position. The locking mechanism may comprise a locking catch or arm formed on one of the third and fourth housing portions. The locking mechanism may comprise a locking recess or notch formed on the other of the third and fourth housing portions configured to engage with the locking catch or arm. The locking mechanism may comprise a clip other suitable mechanical connection.

The first and second housing portions may be hingedly connected by the same hinge member which hingedly connects the third and fourth housing portions.

The housing may comprise at least one alignment feature configured to engage with a corresponding alignment feature of the medicament delivery device to which the hold assistance device is to be attached, to ensure the housing is correctly located on the on the medicament device in use. The alignment feature may be provided on at least one of the first, second, third or fourth housing portions. The alignment feature may comprise one or more projections to be received corresponding one or more recesses in the medicament delivery device. The alignment feature may comprise one or more visual markings, and/or a lip or ledge or other projection or feature configured to abut a feature on medicament delivery device.

The housing may comprise an inner surface and an outer surface. The inner surface may be configured to be fixedly coupled to a medicament delivery device. The alignment feature may be provided on the inner surface of the housing.

The present disclosure also provides a medicament delivery system comprising the hold assistance device described above and a medicament delivery device. The medicament delivery device comprises:

a main body configured to receive a medicament cartridge and comprising a proximal end and a distal end;

a needle for delivery of medicament from the medicament cartridge disposed towards the distal end of the medicament delivery device;

a needle cover axially movable relative to the main body between:

an extended position in which the needle cover extends from the distal end of the main body and covers a distal end of the needle which protrudes from the main body; and a retracted position in which the needle cover is arranged in a proximal position relative to the extended position such that the distal end of the needle protrudes from a distal end of the needle cover, wherein the needle cover comprises at least one aperture or recess towards the distal end of the needle cover;

a needle cover biasing member configured to bias the needle cover axially in the distal direction towards the extended position;

wherein the housing of the hold assistance device is configured to be coupled to the main body, and when the housing is coupled to the main body, the holding element, in the engaged position, is configured to engage with the aperture or recess in the needle cover in its retracted position to resist movement of the needle cover axially in the distal direction towards the extended position.

The hold assistance device may be a separate device to the medicament delivery device and may be attachable and/or attached to the medicament delivery device. Alternatively, the hold assistance device may be integrally formed with the medicament delivery device, for example by being formed integrally with the main body of the medicament delivery device.

The main body of the medicament delivery device may comprise a cut out or recess to receive the or each holding element when in the engaged position.

The medicament delivery system may further comprise a medicament cartridge containing medicament.

The present disclosure also provides a method of operating a medicament delivery system as described above, the method comprising:

coupling the housing to the main body;
moving the needle cover from the extended position to the retracted position; and
moving the holding element into the engaged position such that the holding element engages with the aperture or recess in the needle cover to resist movement of the needle cover axially in the distal direction towards the extended position.

The method may comprise moving the constraining element from the unconstrained position to the constrained position, thereby contacting the holding element and urging the holding element into the engaged position.

The housing may be configured to at least partially circumscribe the main body of a medicament delivery device.

The housing may be configured to be removably coupled to a medicament delivery device.

The housing may be configured to remain stationary relative to a main body of a medicament delivery device.

The step of moving the needle cover from the extended position to the retracted position nay cause the needle cover to retract inside the main body such that the needle is exposed, which may be to place the medicament delivery device in a state ready for medicament to be delivered from the needle to an injection site of a patient.

The step of moving the needle cover from the extended position to the retracted position may comprise placing the medicament delivery device against a surface, for example against the skin of a patient at an injection site, and applying a force in the distal direction towards the surface, thus pushing the needle cover against the surface and causing it to be pushed inside the main body to retract thereinside.

The method may further comprise a step of holding the medicament delivery device for a required duration of time at an injection site of a patient. For example, the method may comprise holding the medicament delivery device at an injection site for the amount of time required for completion of delivery of a medicament from the needle to be complete.

The step of holding the medicament delivery device for a required duration of time at an injection site of a patient may occur after the step of moving the holding element into the engaged position and before the step of moving the holding element into the disengaged position.

BRIEF DESCRIPTION OF THE DRAWINGS

Embodiments will now be described, by way of example only, with reference to the accompanying drawings, in which.

DETAILED DESCRIPTION

Figure 1:
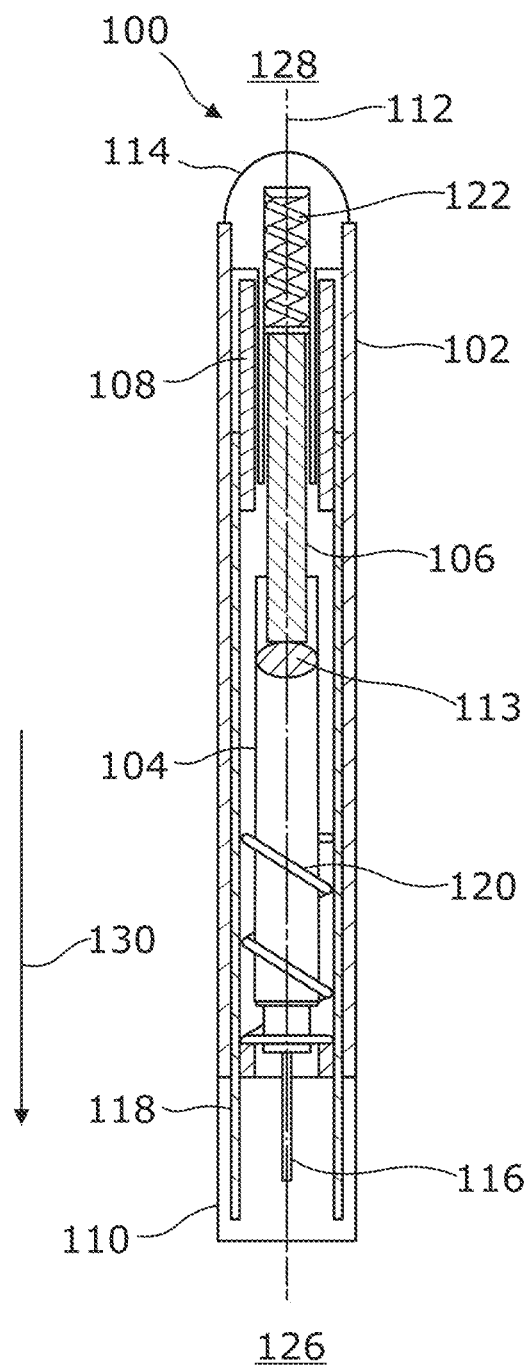
FIG. 1 shows a cross-sectional schematic view of a medicament delivery device.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence medicament delivery. One of these actions may involve a user placing a needle cover (also referred to as a needle shroud or needle sleeve) against an injection site of a subject and applying an axial force to the device to cause the needle cover to retract into the housing of the device. As the needle cover retracts into the housing, the needle of the device extends beyond the needle cover and penetrates the injection site of the subject (e.g. the subject's skin). Medicament delivery may be automatically initiated in response to the retraction of the needle cover or in response to some other action by the user, for example the user pressing a button on the device. Once medicament delivery has been initiated, a medicament delivery mechanism will cause medicament contained within the device to be injected into the subject via the needle. The user should hold the device steady with respect to the injection site during the course of medicament delivery to ensure the needle remains steady within the subject. This is to minimise pain and/or discomfort for the subject, and to prevent a wet injection site, early device removal and/or partial medicament delivery.

After the device is removed from injection site, many autoinjectors cover the needle with the needle cover/needle shroud, which is extended out of the device by a control spring. During activation of the device and while holding the device steady during medicament delivery, the user must counteract the biasing force applied by the control spring to the needle cover. However, some users such as those with impaired dexterity may find it difficult to hold the device steady for a relatively long period of time during medicament delivery. It may be beneficial to provide a device which is easier to handle during medicament delivery. However, simply reducing the biasing force produced by the control spring to the needle cover risks accidental actuation and needle safety issues. Therefore, it is desirable to provide a means to help a user of the device hold the device steady, by reducing the force needed to be applied by the user to overcome the biasing force. It is also desirable to reduce the user hold force, whilst minimising or removing any effect on the inserted needle depth, which can impact on the pharmacokinetic profile of the injected medicament and which does not require, or requires very minimal, casework modifications to the injection device.

FIG. 1 shows a schematic example of a cross section of a medicament delivery device 100 (hereinafter referred to as an injection device) according to one or more aspects of the present disclosure. The injection device 100 is configured to inject a medicament into a subject. The injection device 100 comprises an outer casing 102 (also referred to as a housing or injection device main body) that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. A user typically removes cap 110 from the outer casing 102 before device 100 is operated.

As shown, the outer casing 102 is substantially cylindrical and has a substantially constant diameter along the longitudinal axis of the device 100. The injection device 100 has a distal region 126 and a proximal region 128. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle cover 118 (also referred to as a "needle sleeve" or "needle cover") extend from a distal end of the outer casing 102. The retractable needle cover 118 is biased axially in the distal direction of the injection device 100, for example using a control spring 120, which may also be referred to as a needle cover biasing member 120. The needle cover 118 is coupled to the outer casing 102 to permit axial movement of needle cover 118 relative to the outer casing 102. For example, the cover 118 can move in a longitudinal direction parallel to longitudinal axis 112. Specifically, movement of cover 118 in a proximal direction relative to the outer casing 102 can cause a needle 116 to extend from distal region of the outer casing 102, and outside a distal end of the cover 118.

The plunger 106 is biased towards the distal end of the injection device 100 by a biasing means, for example comprising a drive spring 122. The plunger 106 is retained in an initial position by a combination of the rear casing 114 and the collar 108, preventing the biasing means from displacing the plunger 106 in the distal direction. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 113 in the reservoir 104, displacing the stopper 113 in the distal direction and causing medicament stored in the reservoir 104 to be expelled from the injection device 100 via the needle 116.

Activation of the injection device 100 can occur via several mechanisms. For example, the needle 116 may be fixedly located relative to the outer casing 102 and initially be located within an extended needle cover 118. Proximal movement of the needle cover 118 by placing a distal end of the cover 118 against an injection site of the subject and moving the outer casing 102 in a distal direction will uncover the distal end of the needle 116. Such relative movement allows the distal end of the needle 116 to extend into the injection site. Such insertion is termed "manual" insertion as the needle 116 is manually inserted via the user's manual movement of the outer casing 102 relative to cover 118. Retraction of the cover 118 into the outer casing 102 causes the collar 108 to rotate, releasing the plunger 106.

Another form of activation is "automated", whereby the needle 116 moves relative to the outer casing 102. Such insertion can be triggered by movement of the cover 118 and/or by another form of activation, for example, a user actuation of a button (not shown) of the injection device 100.

Typically, the user presses the needle cover 118 against an injection site to push the needle cover 118 at least partially into the outer casing 102. The exposed needle 116 is pushed into the injection site of the subject. In a holding position, medicament is automatically dispensed from the needle 116 via an automated mechanism. A user must typically hold the needle cover 118 in the holding position for a predetermined period of time, to ensure that the correct dose of medicament is dispensed from the device 100, before removing the device 100 from the injection site.

The spring biasing force 130 from the control spring 120 against which the user must apply a force to move the needle cover 118 is one component of an "activation force" of the device 100. The activation force refers to the force or force profile that the user must exert on the device 100 to move the needle cover 118 from the extended position shown in FIG. 1 to a retracted position within the outer casing 102 for medicament delivery (see for example FIG. 4B). If this force or force profile is not well balanced, it can lead to difficulty in activating the device 100 for some users, or increase the pain or anxiety associated with using the device 100.

Following the injection, the needle 116 can be retracted within the cover 118. Retraction can occur when the cover 118 moves distally under the biasing of the control spring 120, i.e. under the action of the biasing force 130, as a user removes the device 100 from the injection site of the subject. Once a distal end of the cover 118 has moved past a distal end of the needle 116 such that the needle 116 is covered, the cover 118 may be locked in its extended position to prevent any (substantial) proximal movement of the cover 118 relative to the outer casing 102 (i.e., preventing any movement of the cover 118 that would uncover the needle 116). The cover 118 may be locked by a needle cover non-return element (not shown), such as a catch.

Figure 2:
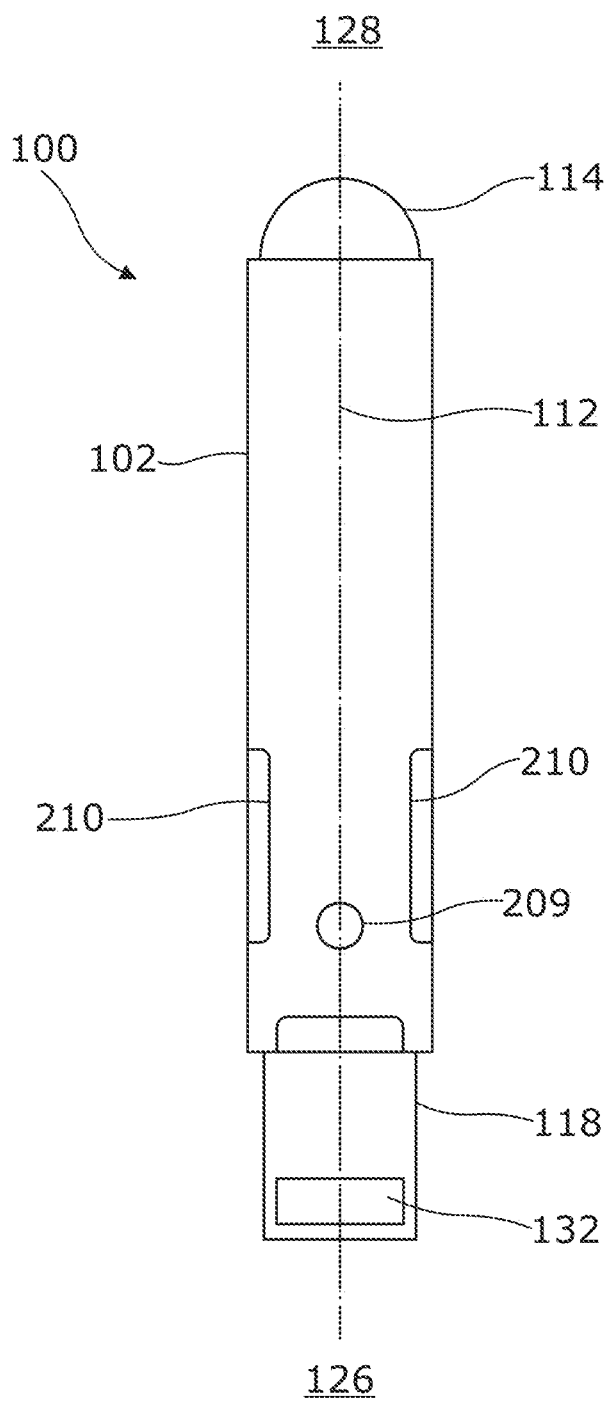
FIG. 2 shows schematic view of a medicament delivery device for use with a hold assistance device of the present disclosure.

FIG. 2 shows a medicament delivery device 100 for use with a hold assistance device 200 of the present disclosure. Features in common with the medicament delivery device shown in FIG. 1 retain the same reference numerals and description thereof will not be repeated. A difference with the medicament delivery device 100 of FIG. 2 is that the needle cover 118 comprises two elongate apertures or cut-outs 132 formed in the distal end of the needle cover 118. The apertures 132 are disposed on diametrically opposite sides of the needle cover 118. Furthermore, recesses 134 are formed in the main body or outer casing 102 at the distal end thereof.

Figure 3:
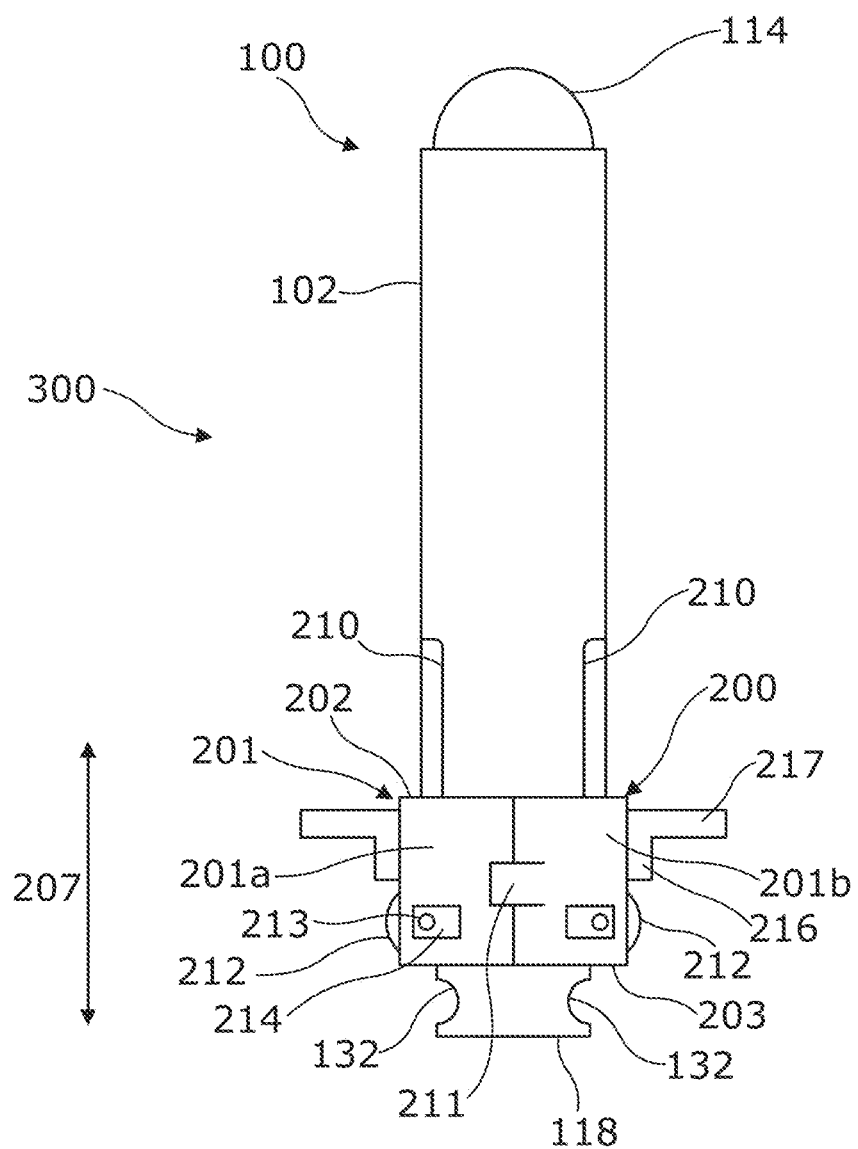
FIG. 3 shows schematic side view of a medicament delivery system comprising a hold assistance device and a medicament delivery device.

FIG. 3 shows a medicament delivery system 300 comprising a medicament delivery device 100 and a hold assistance device 200 coupled to the medicament delivery device 100 proximate the distal end 126 of the medicament delivery device 100. The medicament delivery device 100 may be substantially similar or identical to the injection device 100 shown in FIGS. 1 and/or 2 and described above, in which like reference numerals denote alike elements. In the example shown, the medicament delivery device 100 and the hold assistance device 200 are configured to fit together to form the medicament delivery system 300, such that the hold assistance device 200 is arranged to circumscribe at least a portion of the medicament delivery device 100. The hold assistance device 200 may be configured to be assembled together with the medicament delivery device 100 to be supplied to a user as the medicament delivery system 300, or the hold assistance device 200 and the medicament delivery device 100 may be supplied separately to a user and the user may then assemble the hold assistance device 200 and the medicament delivery device 100 together to form the medicament delivery system 300. It is also envisaged that the hold assistance device 200 may be retrofitted to a medicament delivery device 100, and that the hold assistance device 200 may be used with medicament delivery devices other than that in the example shown in FIG. 1 and described above. It is envisaged that the hold assistance device 200 may be removable from the medicament delivery device 100, such that the hold assistance device 200 may be reusable. The hold assistance device 200 may also be disposable. It is also envisaged that the hold assistance device 200 may be coupled to and formed integrally with a medicament delivery device 100, for example, to be formed integrally with the main body or outer casing 102 of the medicament delivery device 100. The function of the hold assistance device 200 is that it serves to assist the user in the use of the medicament delivery device 100, as outlined below.

Figure 4:
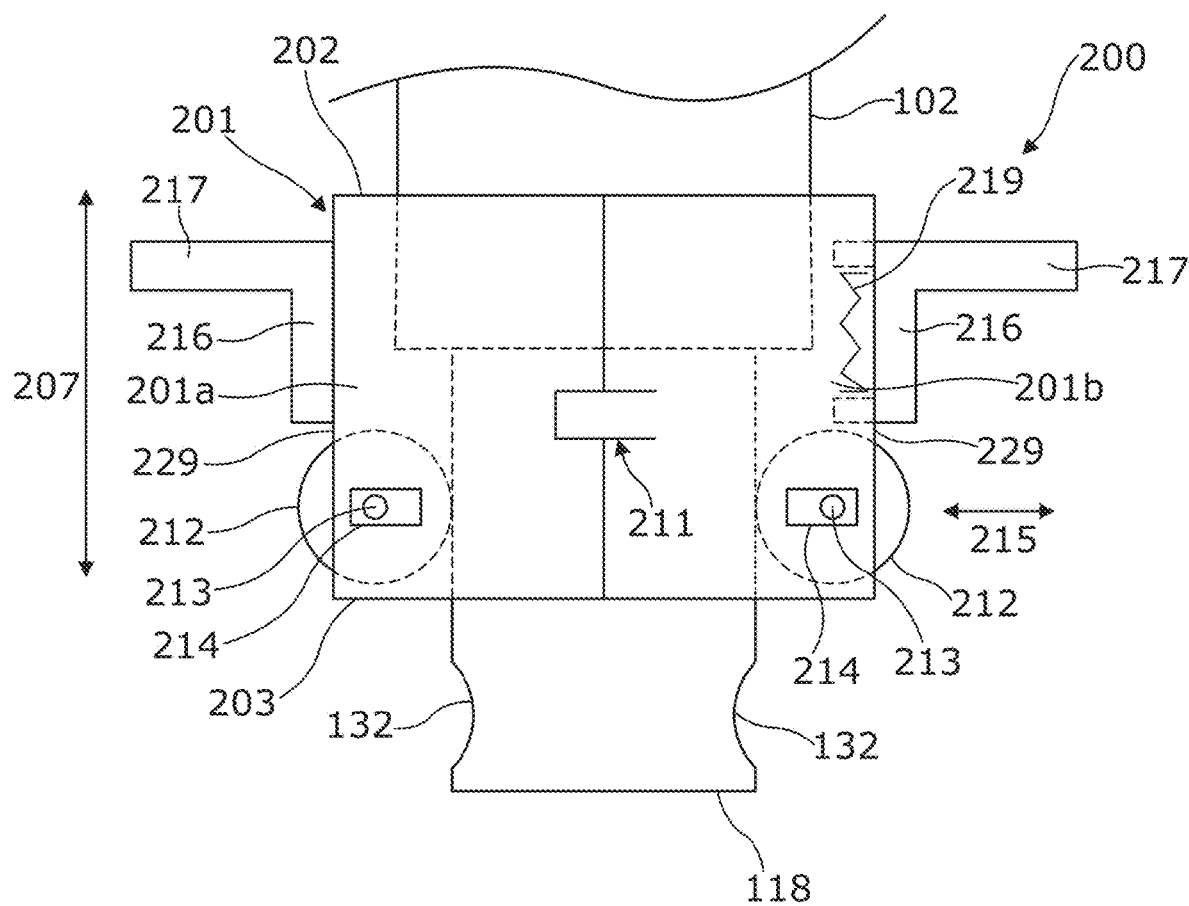
FIG. 4 shows a schematic enlarged side view of a portion of the medicament delivery system of FIG. 3 in a first configuration, with a needle cover in an extended position and holding elements in a disengaged position.

FIG. 4 shows a schematic enlarged side view of a portion of the medicament delivery system 300 in a first configuration. For the sake of clarity and conciseness, only the main body 102 and the needle cover 118 of the medicament delivery device 100 are shown. The needle cover biasing member 120, for example a spring, is arranged to bias the needle cover 118 towards an extended position (see FIGS. 1, 2 and 4 for example) in which the needle cover 118 protrudes from the main body 102 at a distal end 126 of the medicament delivery device 100 such that the needle 116 is covered by the needle cover 118. For example, when the needle cover 118 is in the extended position the needle cover biasing member 120, may for example be a compression spring in its natural extended, uncompressed state, or a state of further extension or lesser compression than when the needle cover 118 is in a more retracted position. Thus, when the needle cover 118 is in a retracted position (see FIG. 5 for example) in which the needle cover 118 is retracted in a proximal position relative to the extended position such that the needle cover 118 is retracted inside the main body 102 and the needle 116 is not covered by the needle cover 118, this acts against the biasing action of the needle cover biasing member 120. For example, where the needle cover biasing member 120 is a compression spring, this causes the needle cover biasing member 120 to be compressed or in a more compressed state than when the needle cover 118 is in the extended position.

Thus, a biasing force 130, for example a spring force 130, which acts in the direction shown in FIG. 1 for example by the arrow 130, will inherently bias the needle cover 118 back towards the extended position shown in FIGS. 1 and 4. That is, because moving the needle cover 118 from the extended position to the retracted position goes against the action of the needle cover biasing member 120, for example by compressing a spring, the needle cover biasing member 120 hence biases the needle cover 118 axially in the distal direction towards the extended position. Thus, once the needle cover 118 has been placed into the retracted position, in order to maintain the needle cover 118 in the retracted position so that the needle 116 remains uncovered and can be used for the required duration of time to deliver medicament to a patient, force is required by the user in order to counteract the biasing force 130, to prevent the needle cover 118 from extending outwards again.

The hold assistance device 200 acts to counteract the biasing force 130, by providing a resistive force thereagainst, in the form of an engagement with the needle cover 118, as described below. In this manner, the hold assistance device 200 reduces the amount of force required from a user to hold the medicament delivery device 100 in a medicament delivery state in which the needle cover 118 is retracted, i.e. reduces the amount of force which needs to be applied by the user to resist the biasing force 130. The hold assistance device 200 does this by engaging the needle cover 118 and thereby resisting its movement under the action of the needle cover biasing member 120 in order to hold the needle cover 118 in the retracted position, to prevent it from inadvertently moving towards the distal end 126 of the medicament delivery device 100, until medicament delivery is complete, at which point the needle cover 118 may be allowed to retract again under the action of the needle cover biasing member 120. In other words, the hold assistance device 200 provides needle cover holding assistance to help offset the user holding force of a standard two-step autoinjector.

Figure 5:
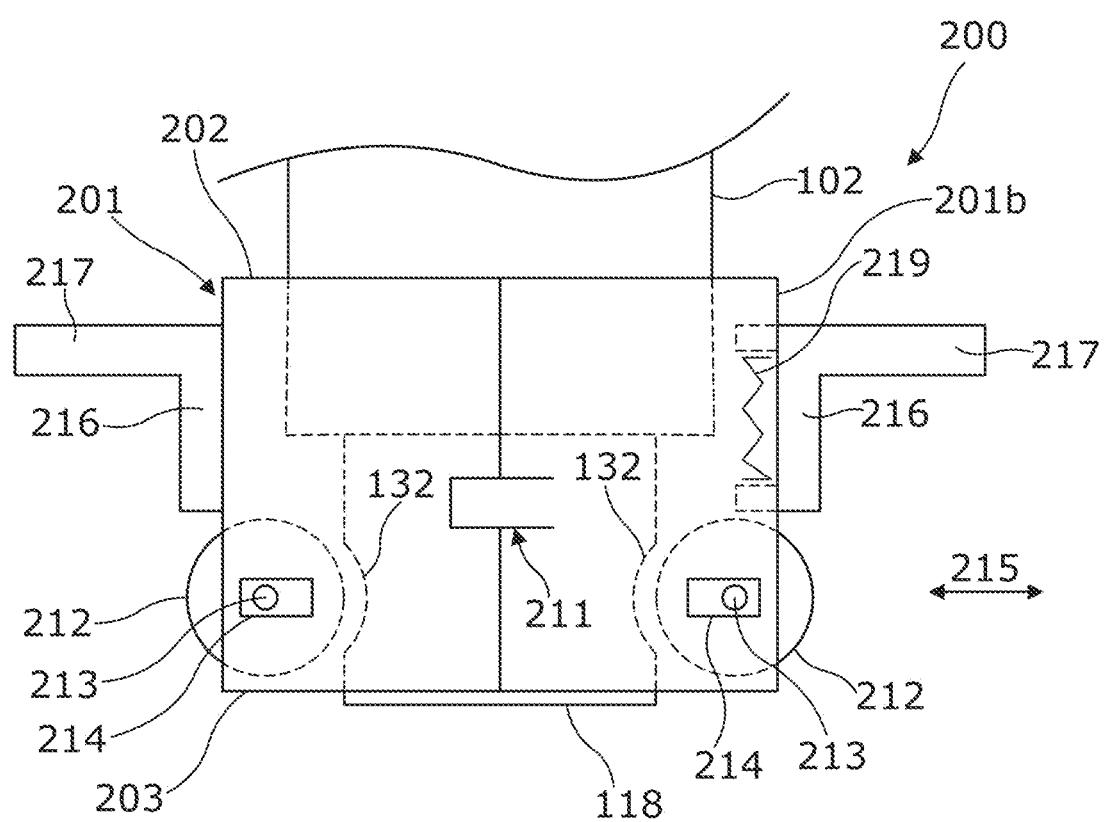
FIG. 5 shows a schematic enlarged side view of a portion of the medicament delivery system of FIG. 3 in a second configuration, with the needle cover in a retracted position and holding elements in a disengaged position.
Figure 6:
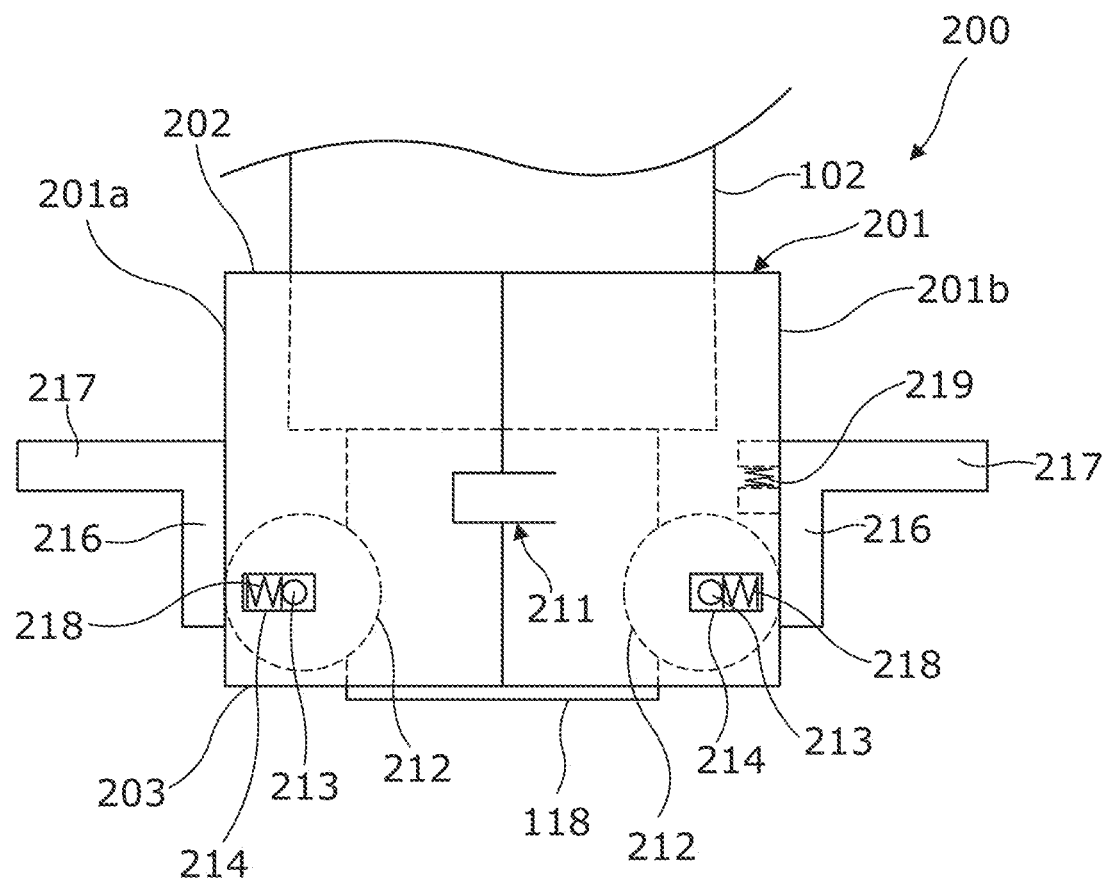
FIG. 6 shows a schematic enlarged side view of a portion of the medicament delivery system of FIG. 3 in a third configuration, with a needle cover in a retracted position and holding elements in an engaged position.
Figure 7:
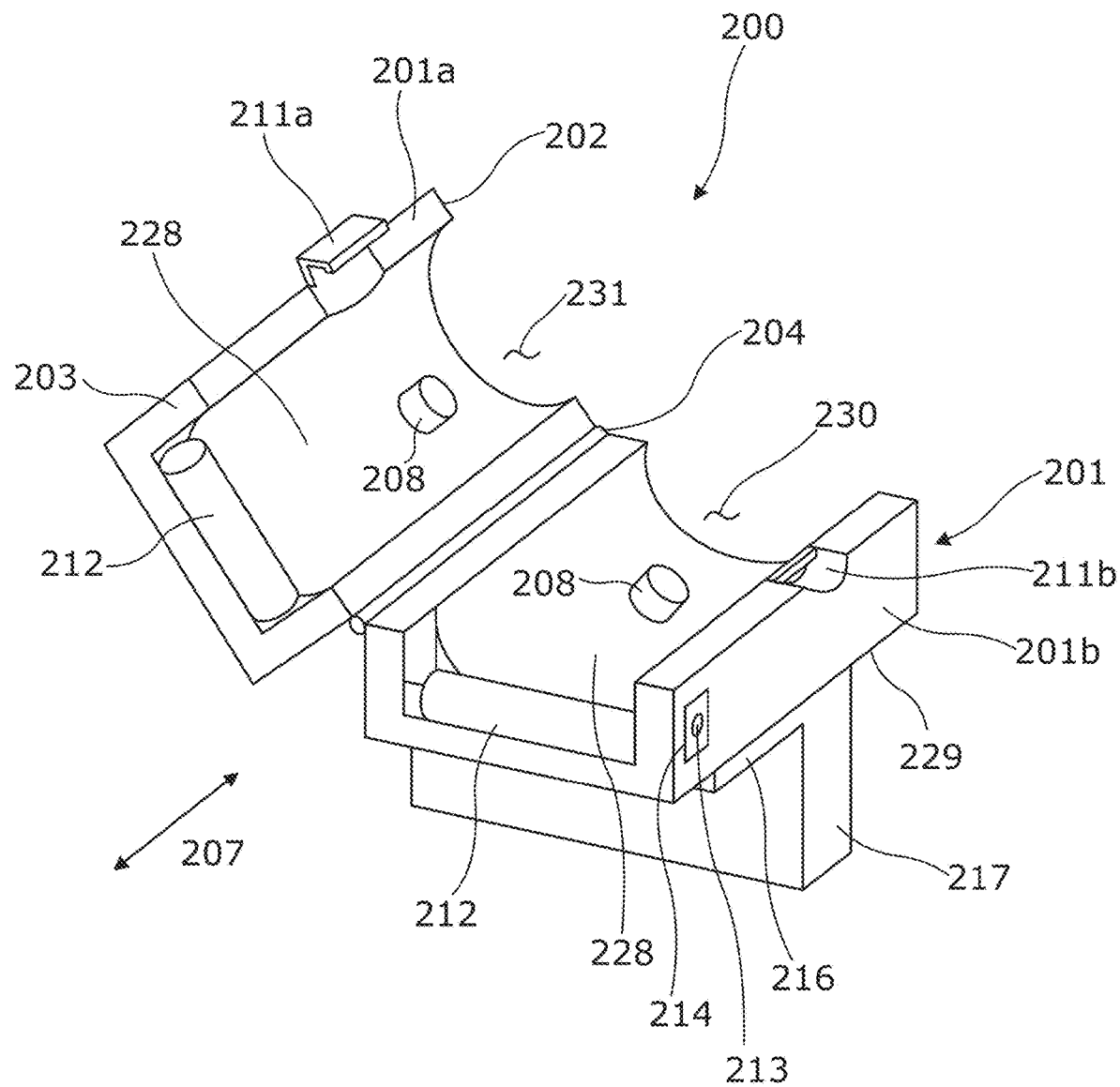
FIG. 7 shows a perspective view of the hold assistance device of FIGS. 3-6 in an opened configuration separate and detached from a medicament delivery device.

Exemplary structures of the hold assistance device 200 which can provide for the resistance against the biasing force 130 shall now be described. FIGS. 4 to 6 show schematic enlarged side view of a portion of the medicament delivery system 300, particularly showing an example of a hold assistance device 200 which is attachable to a medicament delivery device 100 and provides such a resistance against the biasing force 130 of the needle cover biasing member 120 to act against distal movement of the needle cover 118 from the retracted position towards the extended position. FIG. 7 shows a perspective view of the hold assistance device 200 in an opened configuration separate and detached from the medicament delivery device 100. In the example shown, the hold assistance device 200 comprises a housing 201 which is configured to be coupled to the main body 102 of the medicament delivery device 100. The housing 201 comprises first and second housing portions 201a, 201b which are hingedly connected by a housing hinge 204 (see FIG. 7). The housing 201 is thereby configured in a clam-shell type arrangement and moveable between an open position as shown in FIG. 7, where the first and second housing portions 201a, 201b are hinged apart, to a closed configuration, as shown in FIGS. 3-6, where they can clamp around the main body 102 of the medicament delivery device 100. The housing 201 is configured to remain fixed, i.e. stationary, relative to the main body 102—i.e. the housing 201 is not movable relative to the main body 102 when the hold assistance device 200 is coupled to the medicament delivery device 100. The connection between the housing 201 and the main body 102 may though be configured to be removable, such that the hold assistance device 200 may be removed from the medicament delivery device 100.

The housing 201 comprises a proximal end 202 and a distal end 203, which define an axial direction 207. That is, the axial direction 207 is oriented to extend linearly between the proximal end 202 and the distal end 203. Hereinafter, movement in the axial direction 207 away from the distal end 203 and towards the proximal end 202 may be referred to as movement in a proximal direction, and movement in the axial direction 207 away from the proximal end 202 and towards the distal end 203 may be referred to as movement in a distal direction.

The housing 201 may comprise a generally cylindrical passage 230 when in the closed configuration which is arranged to receive and circumscribe the main body 102 of the medicament delivery device 100. In the closed configuration of the housing 201, the passage 230 is generally circumferentially continuous. The passage 230 in the housing 201 is generally cylindrical in order to receive and closely abut against an outer surface of the main body 102 of the medicament delivery device 100 which itself is substantially cylindrical. However, it will be appreciated that the passage 230 in the housing 201 can be configured to any suitable shape to accommodate the main body 102 of the medicament delivery device 100 to which it is intended to be coupled. For example, to accommodate medicament delivery devices 100 with a main body 102 which is oval in cross-section, square or rectangular in cross-section.

The first and second housing portions 201a, 201b comprise an inner surface 228 and an outer surface 229. The inner surface 228 defines an inner surface of the passage 230 and is configured to be fixedly coupled to the medicament delivery device 100 and to interface therewith. That is, the inner surface 228 is arranged to be closer to the main body 102 than the outer surface 229.

In the exemplary embodiment shown, the hold assistance device 200 comprises alignment features 208 which are engageable with cooperating alignment features 209 on the medicament delivery device 100. In the exemplary embodiment shown in FIG. 7, the alignment features 208 on the hold assistance device 200 comprise a protrusion projecting inwardly from the inner surface 228 of each housing portion 201a, 201b. In the medicament delivery device 100 with which the hold assistance device 200 is configured to be used, the alignment features 209 comprise recesses or apertures in the main body 102 (see FIG. 2). These alignment features 208 on the hold assistance device 200 are configured to be received in the recesses or apertures 209 in the main body 102 and thereby locate the hold assistance device 200 in the correct position for it to be fixedly coupled to the medicament delivery device 100 and to function as intended. However, it will be appreciated that alternative forms of alignment features are intended within the scope of the present disclosure, for example, other shaped projections and corresponding recesses one or other of the hold assistance device 200 and medicament delivery device 100, or a projection or lip on the hold assistance device that may locate over a distal end of the main body 102 of the medicament delivery device 100. Furthermore, in some medicament delivery devices 100, a dosing window 210 is provided on the main body 102 to enable the dose of medicament to be viewed during the medicament delivery process, which may additionally assist the user to determine when the complete dose of medicament has been delivered. In some embodiments, the alignment feature(s) 208 on the hold assistance device 200 may be configured to engage with the or each dosing window 210 to correctly locate the hold assistance device 200 on the medicament delivery device 100.

The hold assistance device 200 comprises a locking mechanism 211 to secure the housing 201 in the closed position. In the exemplary embodiment shown, the locking mechanism 211 comprises a locking catch or arm 211a formed on the first housing portion 201a. The locking mechanism 211 also comprises a corresponding locking recess or notch 211b formed on the second housing portion 201b (see FIG. 7). The locking mechanism 211 is operable such that when the housing 201 is fitted around the main body 102 and the first and second housing portions 201a, 201b are moved into the closed position, the locking catch 211a engages with the locking recess and retains the first and second housing portions 201a, 201b in the closed position.

The hold assistance device 200 comprises one or more holding elements which, in the exemplary embodiment shown, comprise a pair of rollers 212. One roller 212 is moveably mounted on each of the first and second housing portions 201a, 201b. The rollers 212 are arranged with their axes generally perpendicular to the axial direction 207 of the housing 201 and with their axes tangential to the main body 102 when the hold assistance device 200 is coupled to the medicament delivery device 100, as shown in FIGS. 3-6. The rollers 212 are provided with a spindle or projecting spindle elements 213 which extend axially from each end of each roller 212. The spindle elements 213 are received in slots 214 in the respective housing portion 201a, 201b. The rollers 212 are thereby arranged such that they are rotatable about the spindle elements 213. The rollers 212 are also moveable in a radial direction relative to the longitudinal axis 112 of the medicament delivery device 100, towards and away from the main body 102 and needle cover 118 (for example, as shown by arrow 215 in FIG. 4). This movement occurs by means of the spindle elements 213 sliding within the slots 214.

The rollers 212 are moveable in the radial direction 215 between a disengaged position (shown in FIGS. 4 and 5) and an engaged position (shown in FIG. 6). In the disengaged position, the rollers 212 are disposed further radially outwardly from the axis 112 of the medicament delivery device 100 than in the engaged position. In the disengaged position, the rollers 212 are spaced sufficiently far apart for the needle cover 118 to pass between them as a clearance or at least sliding contact fit. In the engaged position, the rollers 212 are spaced closer together such that the needle cover 118 cannot freely pass between them. In the retracted position of the needle cover 118 and the engaged position of the rollers 212, the rollers 212 are received within the apertures 132 in the needle cover 118.

The hold assistance device 200 comprises constraining elements which, in the exemplary embodiment shown, comprises a pair of plates 216, one plate 216 being slidably mounted to the outer surface of each housing portion 201a, 201b respectively. The plates 216 are slidable in the axial direction 207 of the housing 201. The plates 216 may be slidably mounted to each housing portion 201a, 201b by any suitable mechanical coupling, for example a projection on one of the plate 216 or housing portion 201a, 201b being received in a slot, groove or recess formed in the other of the plate 216 or housing portion 201a, 201b (not shown). The plates 216 are moveable between an unconstrained position in which the plates 216 are axially spaced from the rollers 212 (as shown in FIGS. 4 and 5) and a constrained position in which the plates 216 are at least axially aligned with the rollers 212 and disposed radially adjacent the rollers 212 (as shown in FIG. 6). In the constrained position, the plates 216 prevent the rollers 212 from moving radially outwardly from their engaged position to their disengaged position, as can be seen from FIG. 6.

The plates 216 of the constraining elements also comprise finger flanges 217 which extend radially outwardly away from the main body 102. In use, the finger flanges 217 are operable by a user to move the plates 216 in an axial distal direction from their unconstrained position to their constrained position. In the exemplary embodiment shown, two finger flanges 217 are provided, although there may be one, or more than two within the scope of the present disclosure. For example, there may be one continuous or part-continuous flange provided around the perimeter or part of the perimeter of the housing 201. In the example shown, the finger flanges 217 are equally spaced apart from one another about the longitudinal axis 112 such that they are diametrically opposed to one another. Though, it is envisaged that the finger flanges 217 may have any other suitable spatial arrangement. In the example shown, each of the finger flanges 217 is integrally formed with or otherwise connected to the plate 216, forming an integral constraining element.

In some embodiments, the plates 216 may be biased towards the unconstrained position, for example by means of a spring or other biasing member 219 (see FIGS. 4-6). In such embodiments, the user would push the plates 216 in the axial distal direction towards the constrained position by pushing the finger flange 217 against the force of such plate 216 biasing member 219. FIGS. 4-6 show only one plate biasing member 219 although it is envisaged within the scope of the present disclosure that each plate 216 may be provided with one, or more than one, such biasing member 219.

FIGS. 3 and 4 show the medicament delivery system 300 in condition before use of the medicament delivery device 100. In the case of a hold assistance device 200 which is detachable from the medicament delivery device 100, it can be seen that the hold assistance device 200 has been attached to the medicament delivery device 100 by the first and second housing portions 201a, 201b being hinged around the main body 102 and secured in place by means of the locking mechanism 211 described above. In this pre-use condition, the rollers 212 are in the disengaged position and the plates 216 are in the unconstrained position. The needle cover 118 is in the extended position before delivery of a medicament from the needle 116 has occurred. The needle cover 118 is thereby a clearance fit from the rollers or at least in sliding contact with the rollers 212 so as to be substantially freely moveable between the rollers 212. Thereby, the needle cover 118 is free to axially slide relative to the main body 102, albeit the needle cover 118 is biased in the distal direction under the action of the biasing force 130 of the needle cover biasing member 120.

When the medicament delivery system 300 is to be used, the user removes the cap 110 to expose needle cover 118 in the extended position shown in FIGS. 3 and 4. The user then places the needle cover 118 on the intended injection site and presses the medicament delivery system 300 in the distal direction. The user may do this by pressing main body 102 in the distal direction, or by pressing the finger flanges 217 in the distal direction. The finger flanges 217 are connected to the housing 201 and the housing 201 is securely connected to the medicament delivery device 100 and so the medicament delivery device 100 is thereby moved in the distal direction towards the injection site. Even if there is some movement of the plates 216 relative to the housing 201, the rollers 212 cannot move radially inwardly due to the presence of the needle cover 118 between the rollers 212 and so the plates 216 would push on the rollers 212 in the distal direction and thereby move the medicament delivery device 100 in the distal direction.

As the medicament delivery system 300 moves in the distal direction, the needle cover 118 presses against the injection site and is moved in the proximal direction against the force of the needle cover biasing member 120 to expose the needle 116 (not shown) to pierce the patient's skin. The needle cover 118 continues to be moved in the proximal direction until the needle cover 118 reaches the retracted position shown in FIG. 5. At this position, the rollers 212 are radially aligned with the apertures 132 in the needle cover 118. The rollers 212 are then able to be moved a radially inward direction 215 to be received within the apertures 132, as shown in FIG. 6. This may be by the user pressing on the finger flanges 217 which moves the plates 216 in the distal direction, and the plates 216 then contacting the outwardly-projecting portion of the rollers 212 and urging the rollers 212 radially inwardly.

In the exemplary embodiment shown each roller 212 is also provided with a roller biasing member, which, in the embodiment shown, may comprise a compression spring 218 (see FIG. 6). Thus, in some embodiments, the rollers 212 may move radially inwardly under the action of the biasing member/spring 218 once the rollers 212 are radially aligned with the apertures 132 in the needle cover 118. However, it will be appreciated that the roller biasing members 218 may be omitted in some embodiments and the rollers 212 may be moved inwardly by the constraining elements/plates 216 moving in the distal direction without the action of additional roller biasing members 218. In embodiments comprising roller biasing members 218, each roller 212 may be provided with two roller biasing members 218. Such roller biasing members 218 may be disposed between the respective housing portion 201a, 201b and the spindle elements 213. Such roller biasing members 218 may act directly on the spindle elements 213, or indirectly on the spindle elements 213, for example via an intermediate component such as a block or sliding contact piece disposed between the roller biasing member 218 and the spindle element 213.

The plates 216 continue to move in the distal direction until they reach the constraining position shown in FIG. 6. In this position, the roller 212 are retained in the apertures 132 in the needle cover 118 and are prevented from moving radially outwardly by the plates 216. Thereby, the rollers 212 being received in the apertures 132 prevents the needle cover 118 from moving from its retracted position towards the extended position under the force of the needle cover biasing member 120. The user is then able to actuate the medicament delivery device 100, or the medicament delivery device 100 may be automatically actuated to deliver the dose of medicament as described above. The position shown in the examples of FIG. 6 may therefore correspond with the time at which a medicament is being injected into a patient. The user is thereby not required to hold the medicament delivery device 100 on the injection site with a hold force against the force of the needle cover biasing member 120 because the hold assistance device 200 prevents the needle cover 118 from moving into its extended position whilst the rollers 212 are located in the apertures 132.

The plates 216 may be kept in the constraining position shown in FIG. 6 for as long as is needed for the user of the medicament delivery system 300 to deliver medicament from the needle 116 of the medicament delivery device 100 to an injection site of a patient, in order to reduce the amount of force needed to be applied by the user to retain the needle cover 118 in the retracted position in which the needle 116 is uncovered and can be used to deliver medicament. After delivery of the medicament from the needle 116 has been completed, the medicament delivery device 100 may be removed from the injection site of the patient, thus the hold force is no longer required. At this point, it may be desirable to recover the needle 116 with the needle cover 118 for safety and hygiene reasons, to help ensure safe removal and disposal of the medicament delivery device 100 from the injection site. Thus, it may be desired to bring the needle cover 118 back into the extended position in which it covers the needle 116. In order to allow the needle cover 118 to revert back into its extended position, under the action of the biasing force 130, needle cover 118 must be released by the hold assistance device 200.

In order to allow the needle cover 118 to move back to its extended position, the plates 216 may be moved out of the constraining position, reversing the steps taken previously, shown in FIG. 5 and then to the position shown in FIG. 4. This may be done manually by the user. In other embodiments envisaged within the scope of the disclosure, the plates 216 may be biased towards the unconstrained position, for example by means of a spring or other biasing member 219. In such embodiments, the user may release pressure on the finger flanges 217 in the axial distal direction to allow the plates 216 to move proximally towards the unconstrained position under the force of such plate biasing member 219. This will enable the rollers 212 to disengage from the apertures 132 and thereby no longer counteract the biasing force 130. The rollers 212 can move out of the apertures 132 under the action of the biasing force 130 on the needle cover 118. In embodiments comprising roller biasing members 218, it is envisaged that the biasing force 130 on the needle cover 118 is sufficient to overcome the biasing force of the roller biasing members 218. The rollers 212 can thereby move in a radially outward direction 215 to the position shown in FIG. 5 so that the needle cover 118 is in a clearance fit or at least in sliding contact with the rollers 212 so as to be substantially freely moveable between the rollers 212. Thereby, the needle cover 118 is free to axially slide relative to the main body 102 in the distal direction under the action of the biasing force 130 of the needle cover biasing member 120. The needle cover 118 then returns to the position shown in FIG. 4, thus safely and hygienically covering the needle 116.

In the above-described exemplary embodiment, the rollers 212 are provided with roller biasing members 218 which act to bias the rollers 212 in a radially inward direction. As the needle cover 118 moves axially relative to the hold assistance device 200, the rollers 212 may roll against the outer surface of the needle cover 118, thereby offering minimal resistance to the axial movement of the needle cover 118. Then when the needle cover 118 reaches the retracted position, the rollers 212 are assistant to automatically move radially inwardly and locate in the apertures 132 under the biasing action of the roller biasing members 218.

However, in alternative embodiments envisaged within the scope of the present disclosure, there may be provided roller biasing members 218 which act to bias the rollers 212 in a radially outward direction. In such embodiments, as the needle cover 118 moves axially relative to the hold assistance device 200, the rollers 212 are biased away from contact with the outer surface of the needle cover 118, thereby minimizing frictional resistance to the axial movement of the needle cover 118. During use of the medicament delivery device 100, as the needle cover 118 moves from the extended to the retracted position, the plates 216 are moved in the distal direction and once the needle cover 118 is in the retracted position, the plates 216 urge the rollers 212 radially inwardly against the force of the roller biasing members 218 into engagement with the apertures 132. Thereafter, once the medicament delivery process is complete and the needle cover 118 moves from the retracted position to the extended position again to recover the needle, the rollers 212 are assistant to automatically move radially outwardly out of engagement with the apertures 132 under the biasing action of the roller biasing members 218. It will be appreciated that both alternative arrangements of roller biasing members 218 can offer advantages to the ease of operation of the medicament delivery system 300 of the present disclosure.

Yet further, it is envisaged within the scope of the present disclosure, the hold assistance device may be provided without roller biasing members 218. In such embodiments, as the needle cover 118 moves axially relative to the hold assistance device 200, the rollers 212 are either spaced from or roll in slight contact with the outer surface of the needle cover 118, with minimal frictional resistance to the axial movement of the needle cover 118. During use of the medicament delivery device 100, as the needle cover 118 moves from the extended to the retracted position, the plates 216 are moved in the distal direction and once the needle cover 118 is in the retracted position, the plates 216 urge the rollers 212 radially inwardly be action of the plates 216 alone and into engagement with the apertures 132. Thereafter, once the medicament delivery process is complete and the needle cover 118 moves from the retracted position to the extended position again to recover the needle, the rollers 212 are moved radially outwardly out of engagement with the apertures 132 under the biasing force 130 of the needle cover biasing member 120. It will be appreciated that such an arrangement may offer an advantage of ease, simplicity and reduced cost of construction and manufacture of the medicament delivery system 300 of the present disclosure.

Figure 8:
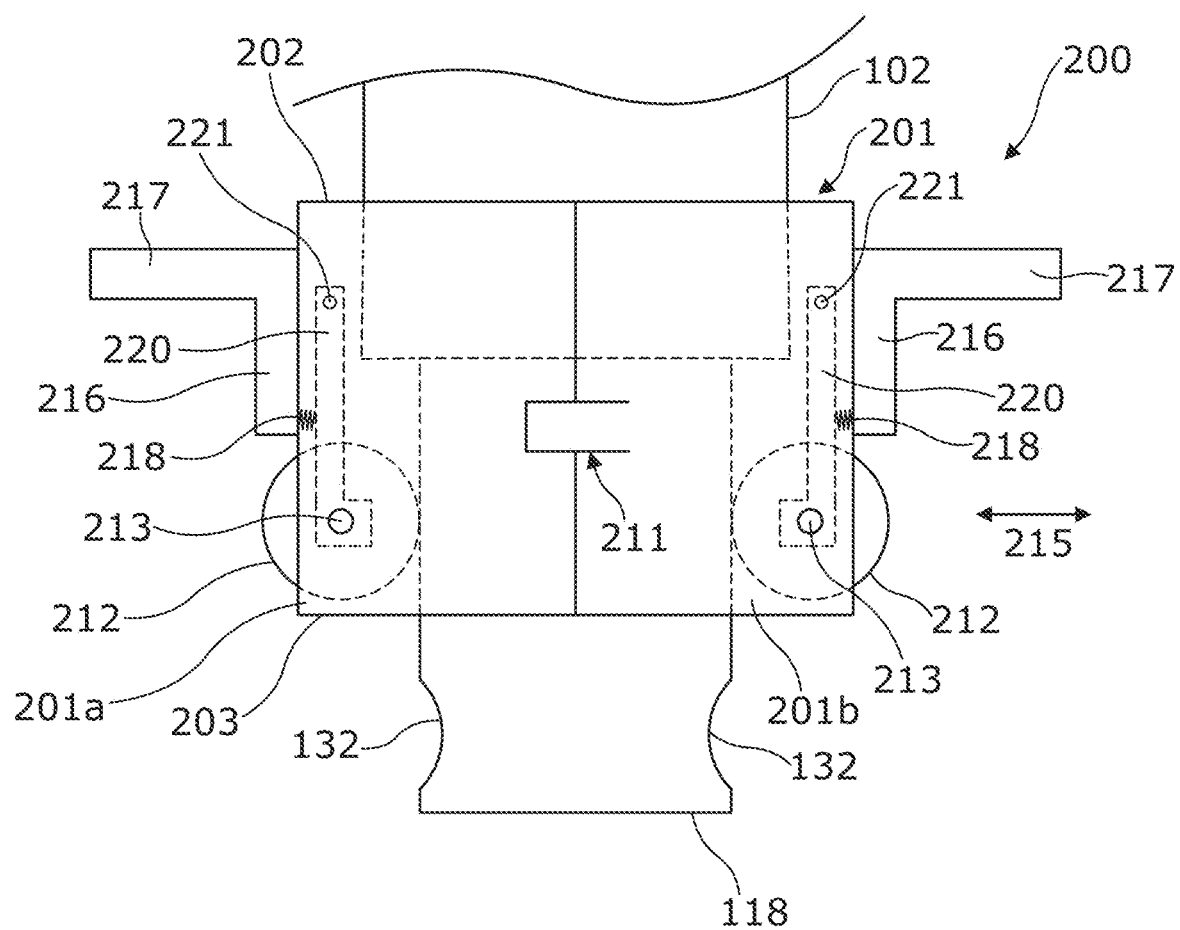
FIG. 8 shows a schematic enlarged side view of a portion of a medicament delivery system similar to that of FIG. 3 but with a hold assistance device of another embodiment of the present disclosure in a first configuration, with the needle cover in an extended position and holding elements in a disengaged position.
Figure 9:
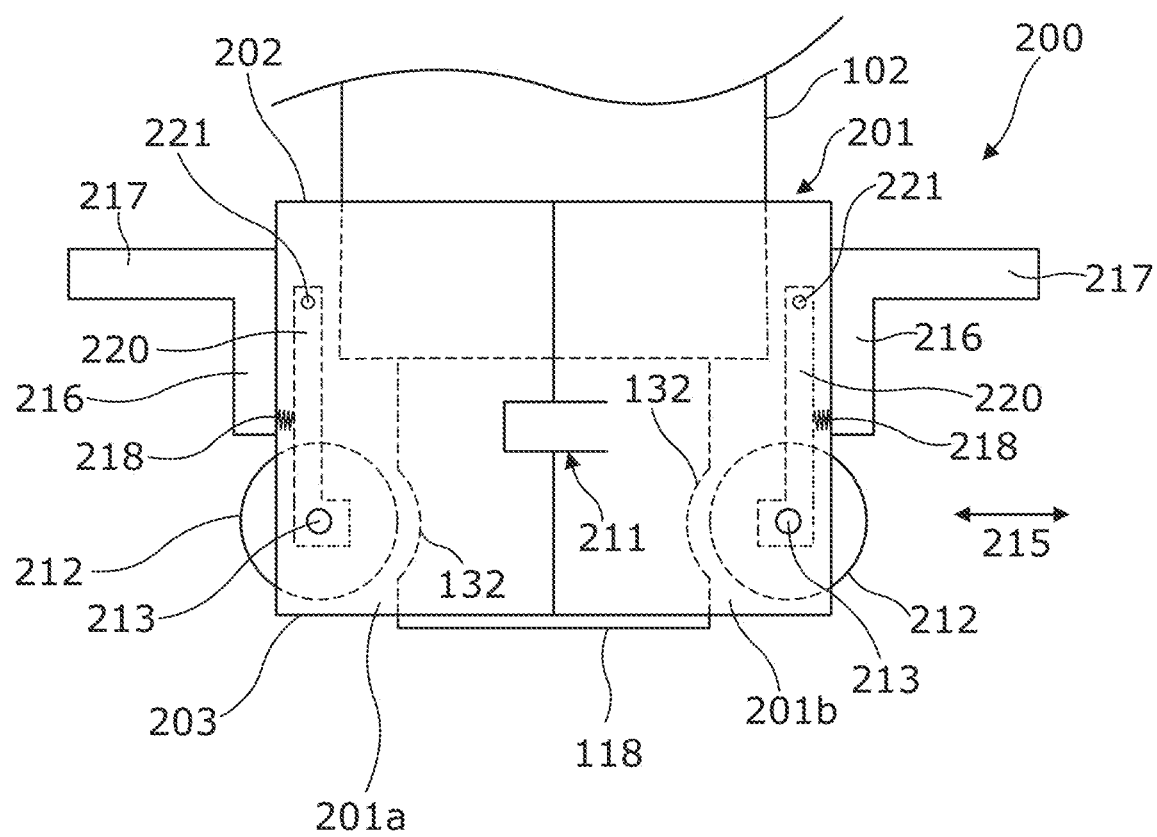
FIG. 9 shows a schematic enlarged side view of a portion of the medicament delivery system of FIG. 8 in a second configuration, with the needle cover in a retracted position holding elements in a disengaged position.
Figure 10:
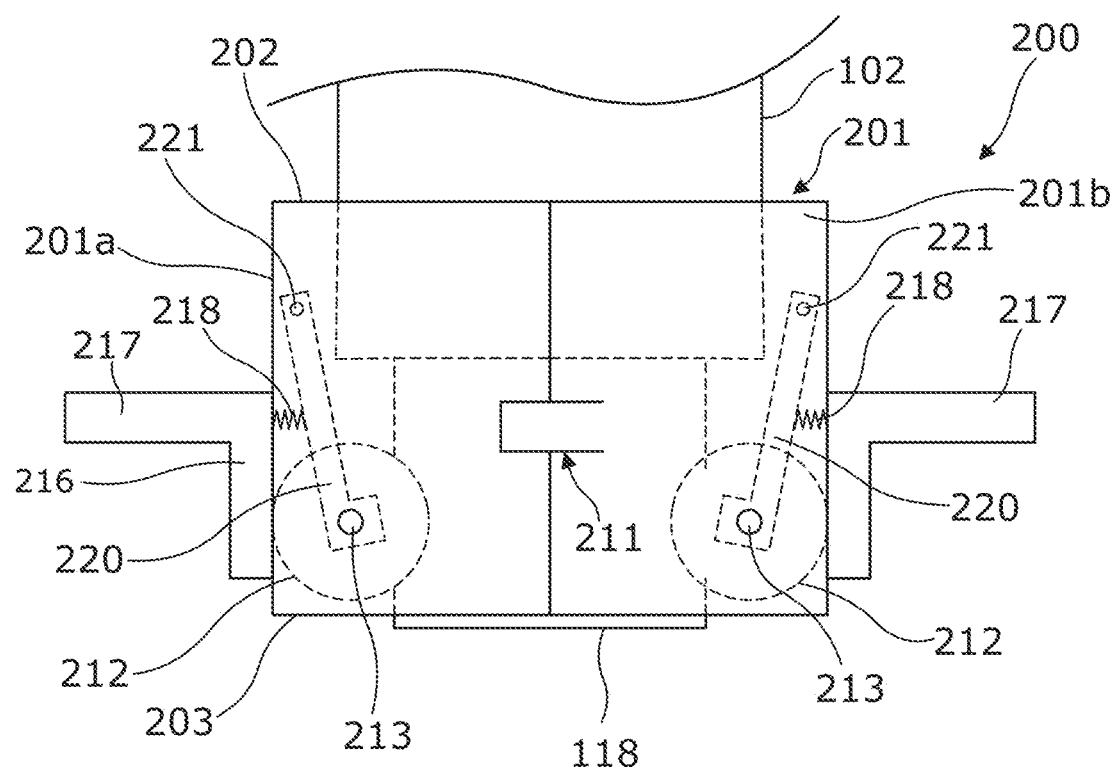
FIG. 10 shows a schematic enlarged side view of a portion of the medicament delivery system of FIGS. 8 and 9 in a third configuration, with the needle cover in a retracted position and holding elements in an engaged position.

FIGS. 8-10 show schematic enlarged side views of a portion of a medicament delivery system 300 similar to that of FIG. 3 and FIGS. 4-6, but comprising a medicament delivery device 100 and a hold assistance device 200 of another embodiment of the present disclosure. Like features in common with the previously-described embodiment of hold assistance device 200 retain the same reference numerals and will not be described in detail again.

A difference with the embodiment shown in FIGS. 8-10 is that the holding elements which, in the exemplary embodiment, comprise rollers 212, are provided on arms 220 pivotally attached to each respective housing portion 201a, 201b at pivots 221. In embodiments of the present disclosure, one or more than one arm 220 may be provided for each roller 212. The rollers 212 thereby are moveable in the radial direction 215 between the disengaged position (shown in FIGS. 8 and 9) and the engaged position (shown in FIG. 10) by the arms 220 pivoting about the pivot points 221. As in the previously-described embodiment, in the disengaged position, the rollers 212 are disposed further radially outwardly from the axis 112 of the medicament delivery device 100 than in the engaged position. In the disengaged position, the rollers 212 are spaced sufficiently far apart for the needle cover 118 to pass between them as a clearance or at least sliding contact fit. In the engaged position, the rollers 212 are spaced closer together such that the needle cover 118 cannot freely pass between them. In the retracted position of the needle cover 118 and the engaged position of the rollers 212, the rollers 212 are received within the apertures 132 in the needle cover 118.

The hold assistance device 200 comprises constraining elements which, in the exemplary embodiment shown, comprises a pair of plates 216 with finger flanges 217 with the same function and configuration as described previously, which again, may in some embodiments be biased towards the unconstrained position, for example by means of a spring or other biasing member 219 as shown in FIGS. 4-6.

FIGS. 8 and 9 show the medicament delivery system 300 in condition before use of the medicament delivery device 100. In the case of a hold assistance device 200 which is detachable from the medicament delivery device 100, it can be seen that the hold assistance device 200 has been attached to the medicament delivery device 100 by the first and second housing portions 201a, 201b being hinged around the main body 102 and secured in place by means of the locking mechanism 211 described above. In this pre-use condition, the rollers 212 are in the disengaged position and the plates 216 are in the unconstrained position.

When the medicament delivery system 300 is to be used, the user removes the cap 110 to expose needle cover 118 in the extended position shown in FIGS. 3 and 8, places the needle cover 118 on the intended injection site and presses the medicament delivery system 300 in the distal direction as described previously. The needle cover 118 presses against the injection site, is moved in the proximal direction against the force of the needle cover biasing member 120 and continues to be moved in the proximal direction until the needle cover 118 reaches the retracted position shown in FIG. 9. At this position, the rollers 212 are radially aligned with the apertures 132 in the needle cover 118. The rollers 212 are then able to be moved a radially inward direction 215 to be received within the apertures 132, as shown in FIG. 9. This may be by the user pressing on the finger flanges 217 which moves the plates 216 in the distal direction, and the plates 216 then contacting the outwardly-projecting portion of the rollers 212 and urging the rollers 212 radially inwardly.

In the exemplary embodiment shown in FIGS. 8-10, each roller 212 is also provided with a roller biasing member, which, in the embodiment shown, may comprise a compression spring 218 acting on the arm 220. Thus, in some embodiments, the rollers 212 may move radially inwardly under the action of the biasing member/spring 218 once the rollers 212 are radially aligned with the apertures 132 in the needle cover 118. However, it will be appreciated that the roller biasing members 218 may be omitted in some embodiments and the rollers 212 and arms 220 may be moved inwardly by the constraining elements/plates 216 moving in the distal direction without the action of additional roller biasing members 218.

The plates 216 continue to move in the distal direction until they reach the constraining position shown in FIG. 10. In this position, the roller 212 are retained in the apertures 132 in the needle cover 118 and are prevented from moving radially outwardly by the plates 216 with the resulting needle cover 118 movement prevention and hold force reduction as described previously. Furthermore, after delivery of the medicament, in order to allow the needle cover 118 to move back to its extended position, the plates 216 may be moved out of the constraining position, reversing the steps taken previously. Again, this may be done manually by the user or in other embodiments, the plates 216 may be biased towards the unconstrained position, for example by means of a spring or other biasing member 219 as described above. In embodiments comprising roller biasing members 218, it is envisaged that the biasing force 130 on the needle cover 118 is sufficient to overcome the biasing force of the roller biasing members 218. The rollers 212 can thereby move in a radially outward direction 215 to the position shown in FIG. 9 so that the needle cover 118 is substantially freely moveable between the rollers 212 and can return to the position shown in FIG. 8, thus safely and hygienically covering the needle 116.

As with the previously-described embodiment, the rollers 212 are provided with roller biasing members 218 which act to bias the rollers 212 in a radially inward direction with the functional benefit described above. However, in alternative embodiments envisaged within the scope of the present disclosure, there may be provided roller biasing members 218 which act to bias the rollers 212 and arms 220 in a radially outward direction, again with the alternative functional advantages described above. Yet further, it is envisaged within the scope of the present disclosure that the hold assistance device 200 may be provided without roller 212/arm 220 biasing members 218, with the same functional and constructional advantages of such configuration as described above.

Figure 11:
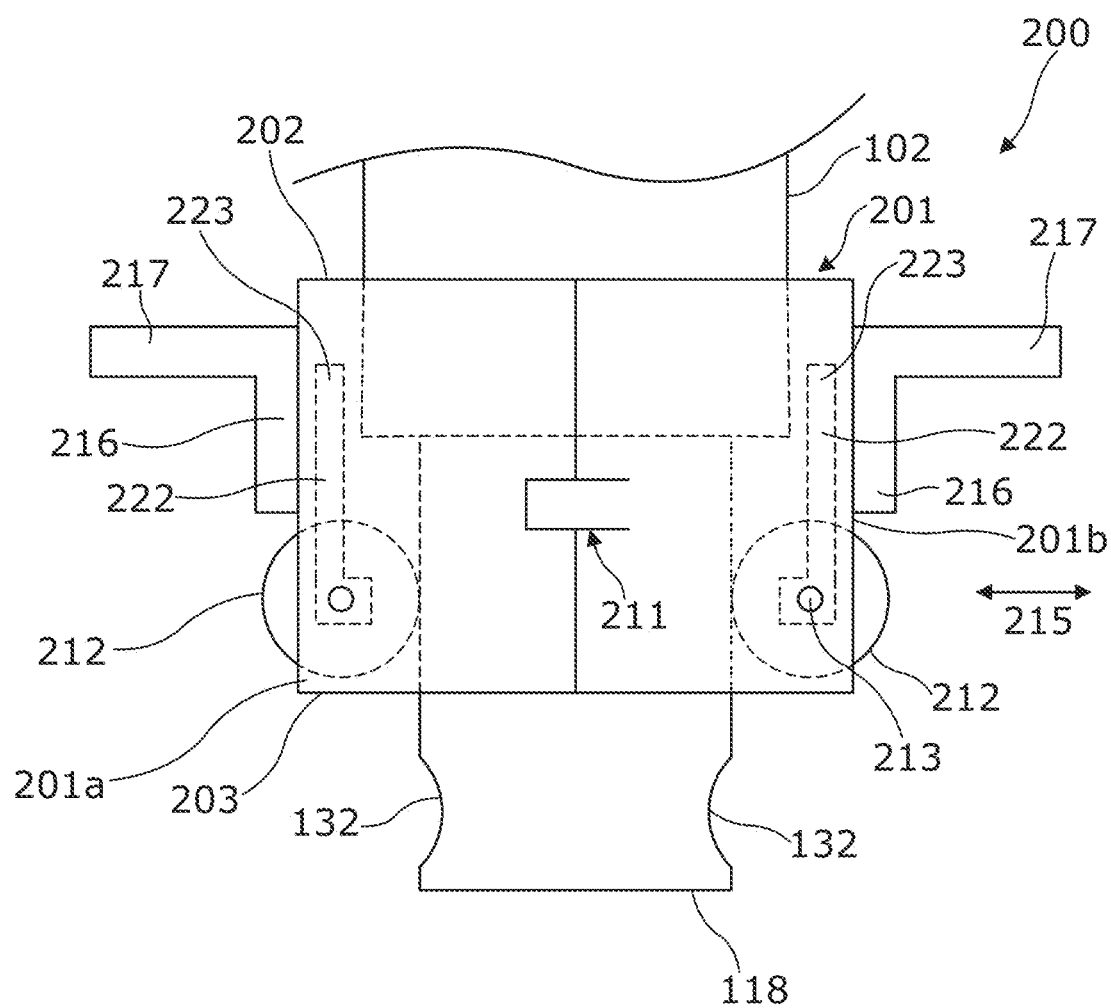
FIG. 11 shows a schematic enlarged side view of a portion of a medicament delivery system similar to that of FIG. 3 but with a hold assistance device of another embodiment of the present disclosure in a first configuration, with the needle cover in an extended position and holding elements in a disengaged position.
Figure 12:
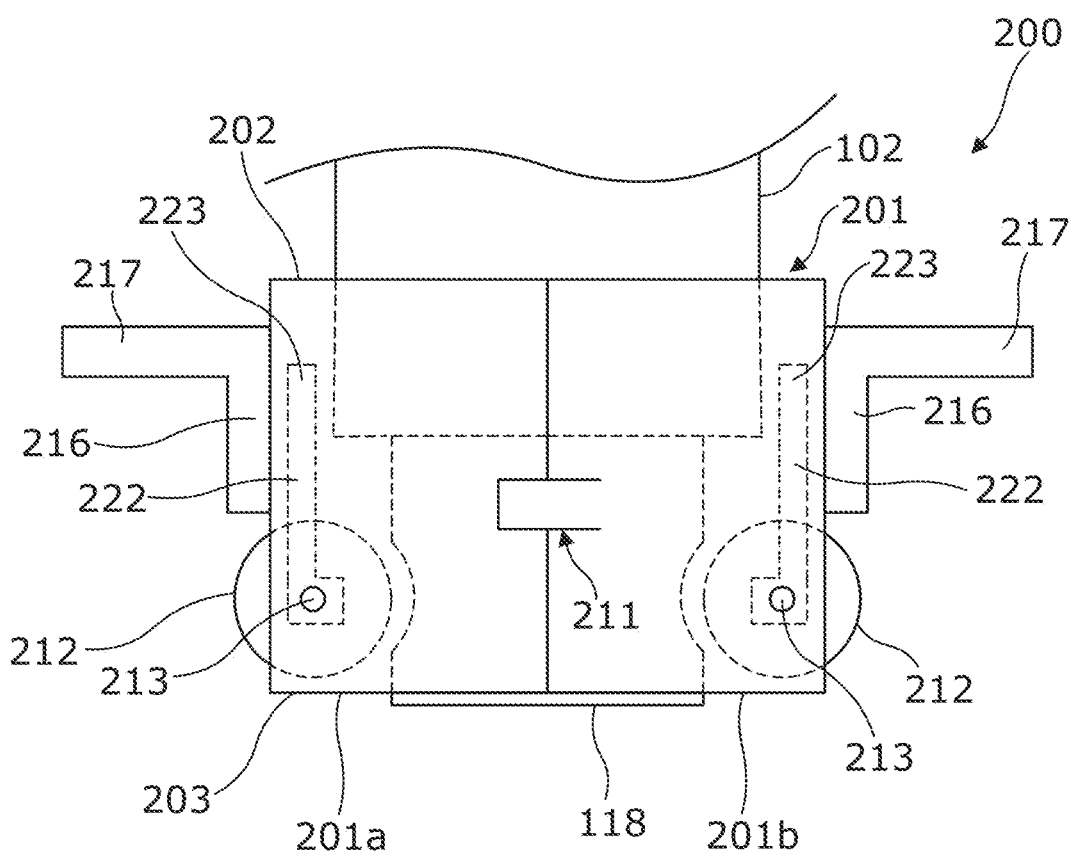
FIG. 12 shows a schematic enlarged side view of a portion of the medicament delivery system of FIG. 11 in a second configuration, with the needle cover in a retracted position the holding elements in a disengaged position.
Figure 13:
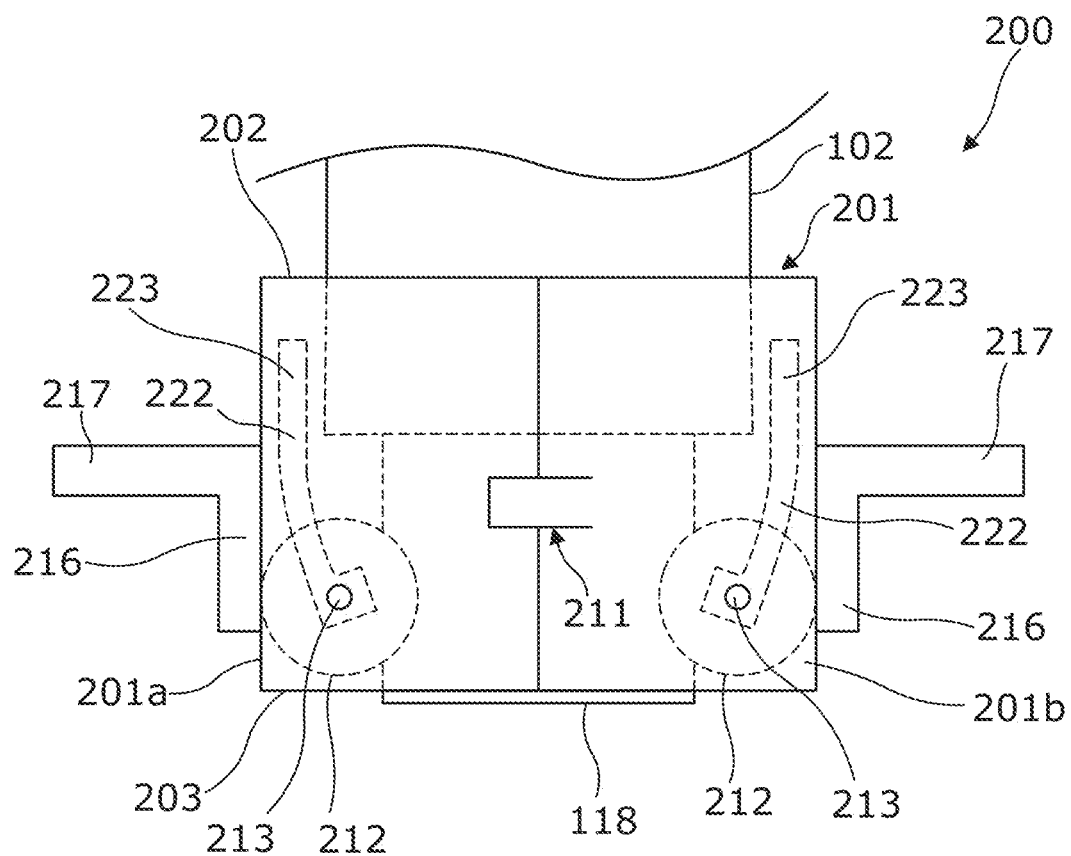
FIG. 13 shows a schematic enlarged side view of a portion of the medicament delivery system of FIGS. 11 and 12 in a third configuration, with the needle cover in a retracted position and holding elements in an engaged position.

FIGS. 11-13 show schematic enlarged side views of a portion of a medicament delivery system 300 similar to that of FIG. 3 and FIGS. 4-6 and 8-10, but comprising a medicament delivery device 100 and a hold assistance device 200 of another embodiment of the present disclosure. Like features in common with the previously-described embodiments of hold assistance devices 200 retain the same reference numerals and will not be described in detail again.

A difference with the embodiment shown in FIGS. 11-13 is that the holding elements which, in the exemplary embodiment, comprise rollers 212, are provided on resiliently flexible arms 222 which are fixedly attached to each respective housing portion 201a, 201b at fixed points 223. Such arms 222 may be integrally formed with the respective housing portion 201a, 201b, or may be otherwise fixedly attached to the respective housing portion 201a, 201b, for example by mechanical connection or bonding. In embodiments of the present disclosure, one or more than one arm 222 may be provided for each roller 212. The arms 222 are resiliently deformable as they flex between an undeformed, disengaged position (shown in FIGS. 11 and 12) and a deformed, engaged position (shown in FIG. 13). The rollers 212 thereby are moveable in the radial direction 215 between the disengaged position and the engaged position as the arms 222 resiliently deform about the fixed points 223. As in the previously-described embodiment, in the disengaged position, the rollers 212 are disposed further radially outwardly from the axis 112 of the medicament delivery device 100 than in the engaged position. In the disengaged position, the rollers 212 are spaced sufficiently far apart for the needle cover 118 to pass between them as a clearance or at least sliding contact fit. In the engaged position, the rollers 212 are spaced closer together such that the needle cover 118 cannot freely pass between them. In the retracted position of the needle cover 118 and the engaged position of the rollers 212, the rollers 212 are received within the apertures 132 in the needle cover 118.

The hold assistance device 200 comprises constraining elements which, in the exemplary embodiment shown, comprises a pair of plates 216 with finger flanges 217 with the same function and configuration as described previously, which again, may in some embodiments be biased towards the unconstrained position, for example by means of a spring or other biasing member 219 as shown in FIGS. 4-6.

FIGS. 11 and 12 show the medicament delivery system 300 in condition before use of the medicament delivery device 100. In the case of a hold assistance device 200 which is detachable from the medicament delivery device 100, it can be seen that the hold assistance device 200 has been attached to the medicament delivery device 100 by the first and second housing portions 201a, 201b being hinged around the main body 102 and secured in place by means of the locking mechanism 211 described above. In this pre-use condition, the rollers 212 are in the disengaged position and the plates 216 are in the unconstrained position.

When the medicament delivery system 300 is to be used, the user removes the cap 110 to expose needle cover 118 in the extended position shown in FIGS. 3 and 11, places the needle cover 118 on the intended injection site and presses the medicament delivery system 300 in the distal direction as described previously. The needle cover 118 presses against the injection site, is moved in the proximal direction against the force of the needle cover biasing member 120 and continues to be moved in the proximal direction until the needle cover 118 reaches the retracted position shown in FIG. 12. At this position, the rollers 212 are radially aligned with the apertures 132 in the needle cover 118. The rollers 212 are then able to be moved a radially inward direction 215 to be received within the apertures 132, as shown in FIG. 12. This may be by the user pressing on the finger flanges 217 which moves the plates 216 in the distal direction, and the plates 216 then contacting the outwardly-projecting portion of the rollers 212 and urging the rollers 212 radially inwardly.

In the exemplary embodiment shown in FIGS. 11-13, the resilient arms 222 are elastically deformable such that movement of the rollers 212 in the inwardly radial direction is against the force of elastic deformation of the flexible arms 222. Thus, in some embodiments, the rollers 212 may move radially inwardly against the resilient resistance of the flexible arms 222 once the rollers 212 are radially aligned with the apertures 132 in the needle cover 118.

The plates 216 continue to move in the distal direction until they reach the constraining position shown in FIG. 13. In this position, the roller 212 are retained in the apertures 132 in the needle cover 118 and are prevented from moving radially outwardly by the plates 216 with the resulting needle cover 118 movement prevention and hold force reduction as described previously. Furthermore, after delivery of the medicament, in order to allow the needle cover 118 to move back to its extended position, the plates 216 may be moved out of the constraining position, reversing the steps taken previously. Again, this may be done manually by the user or in other embodiments, the plates 216 may be biased towards the unconstrained position, for example by means of a spring or other biasing member 219 as described above. In the exemplary embodiment shown, the resilient of the flexible arms 222 would urge the rollers 212 radially outwardly towards the disengaged position. This would also be assisted by the biasing force 130 on the needle cover 118 moving the rollers 212 in a radially outward direction 215 to the position shown in FIG. 12 so that the needle cover 118 is substantially freely moveable between the rollers 212 and can return to the position shown in FIG. 11, thus safely and hygienically covering the needle 116.

In the embodiment shown in FIGS. 11-13, the elastic resilience of the flexible arms 222 acts to bias the rollers 212 in a radially outward direction with the functional benefit described above in embodiments in which the roller biasing members 218 urge the rollers 212 in a radially outward direction. However, in alternative embodiments envisaged within the scope of the present disclosure, there may be provided flexible arms 222 configured such that the arms 222 are in a more relaxed condition when the rollers 212 are in the engaged position, and an elastically deformed condition when the rollers are in the disengaged position, such that the flexible arms 222 are configured to bias the rollers 212 radially inwardly towards the engaged position. Such embodiment would also then provide the alternative functional advantages described above with reference to embodiments in which the roller biasing members 218 urge the rollers 212 radially inwardly.

Figure 14:
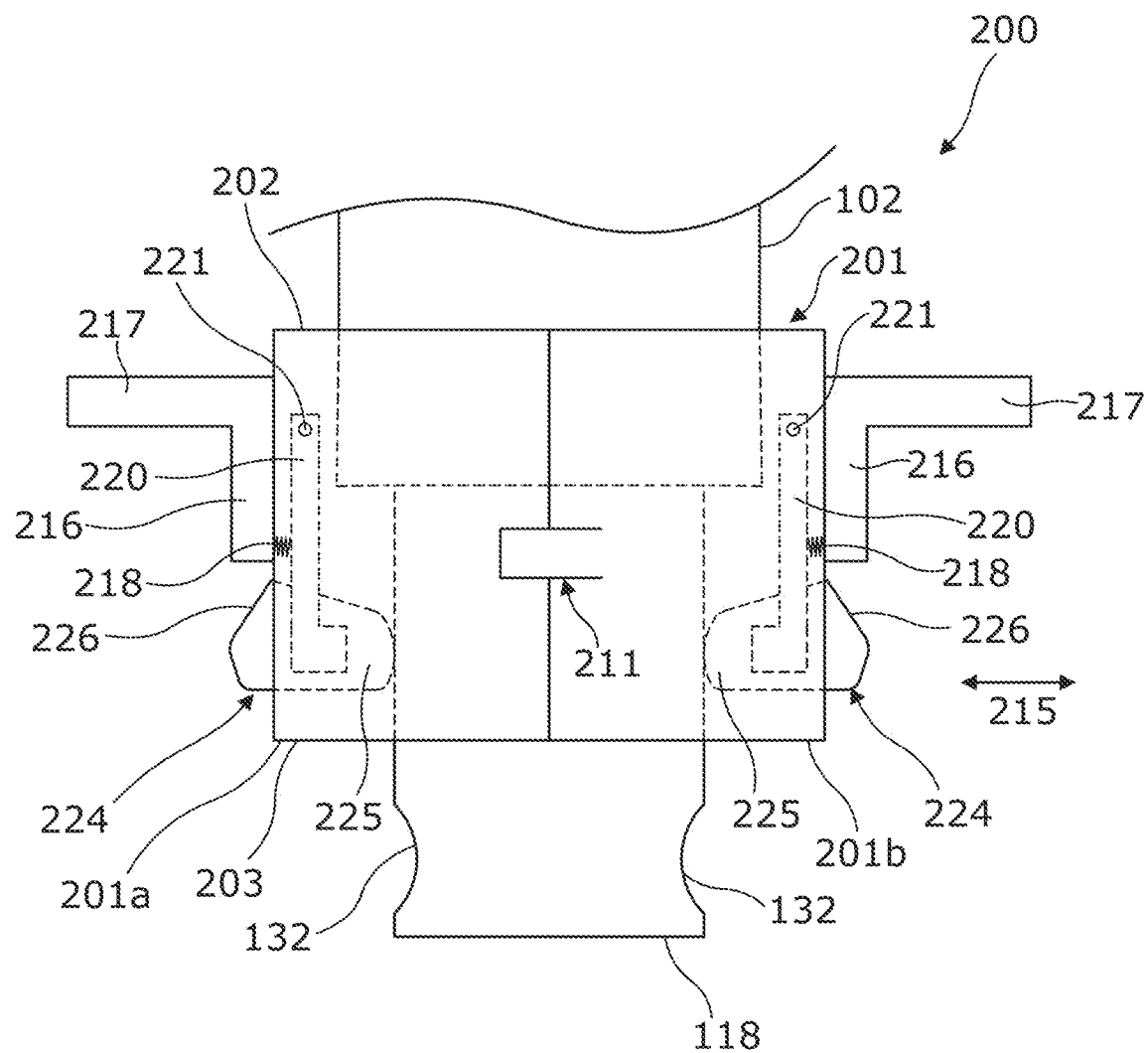
FIG. 14 shows a schematic enlarged side view of a portion of a medicament delivery system similar to that of FIG. 3 but with a hold assistance device of another embodiment of the present disclosure in a first configuration, with the needle cover in an extended position and holding elements in a disengaged position.
Figure 15:
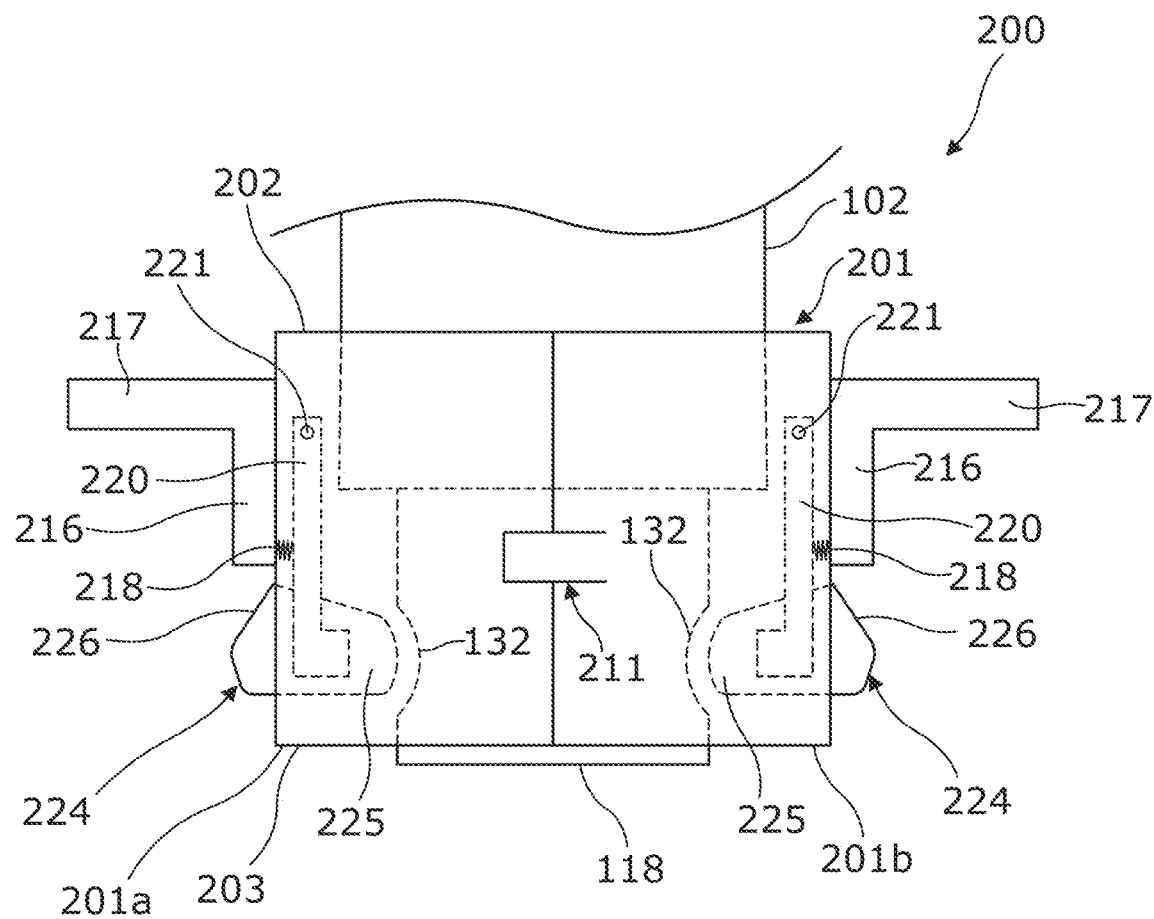
FIG. 15 shows a schematic enlarged side view of a portion of the medicament delivery system of FIG. 14 in a second configuration, with the needle cover in a retracted position the holding elements in a disengaged position.
Figure 16:
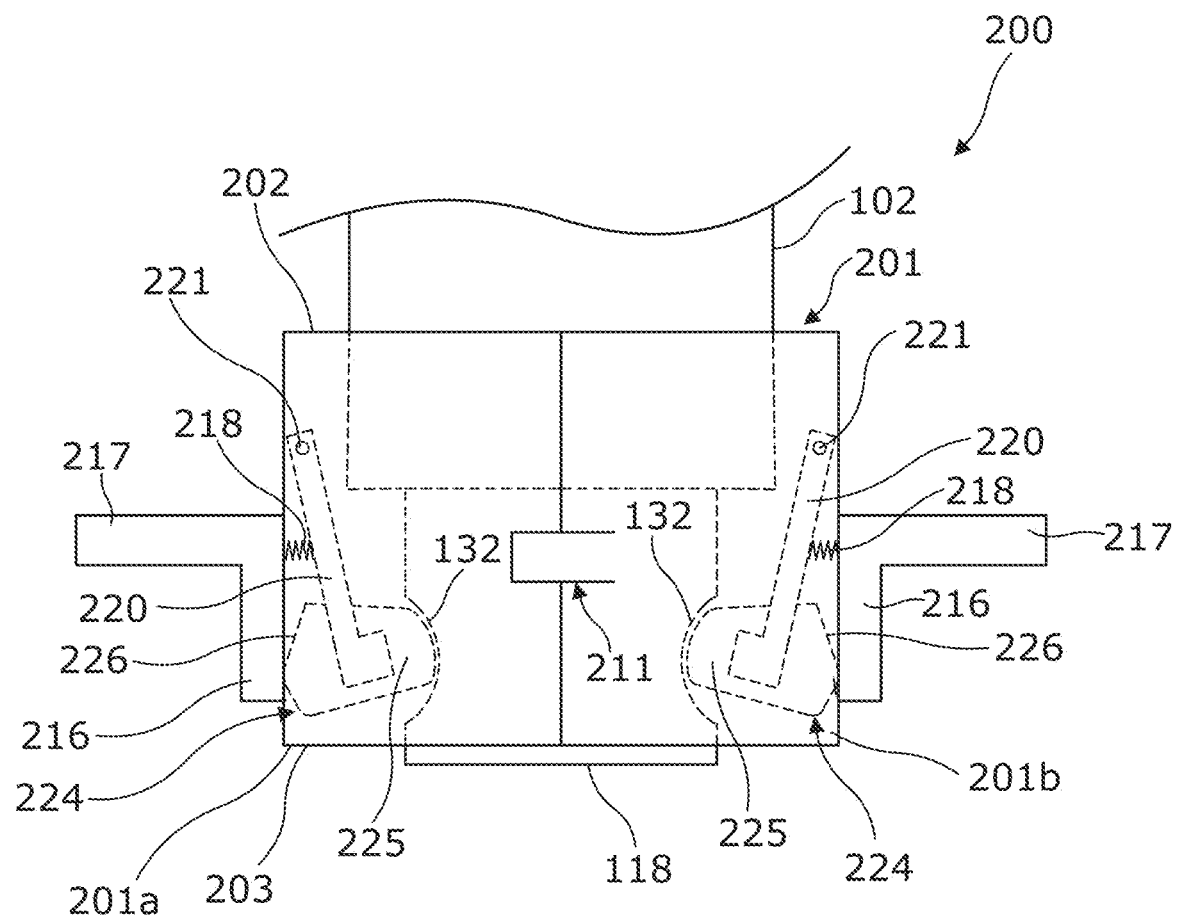
FIG. 16 shows a schematic enlarged side view of a portion of the medicament delivery system of FIGS. 14 and 15 in a third configuration, with the needle cover in a retracted position and holding elements in an engaged position.

FIGS. 14-16 show schematic enlarged side views of a portion of a medicament delivery system 300 similar to that of FIG. 3 and FIGS. 4-6, 8-10 and 11-13, but comprising a medicament delivery device 100 and a hold assistance device 200 of another embodiment of the present disclosure. Like features in common with the previously-described embodiment of hold assistance device 200 retain the same reference numerals and will not be described in detail again.

A difference with the embodiment shown in FIGS. 14-16 is that the holding elements are not rollers but are fixed elements 224 which comprise a radially-inward protrusion 225. As with the embodiment of FIGS. 8-10, these fixed elements 224 are provided on arms 220 pivotally attached to each respective housing portion 201a, 201b at pivots 221. The same features of the arms 220 as described previously apply to the embodiment of FIGS. 14-16 and so will not be described in detail again. However, the fixed elements 224 are thereby moveable in the radial direction 215 between the disengaged position (shown in FIGS. 14 and 15) and the engaged position (shown in FIG. 16) by the arms 220 pivoting about the pivot points 221.

The hold assistance device 200 comprises constraining elements which, in the exemplary embodiment shown, comprises a pair of plates 216 with finger flanges 217 with the same function and configuration as described previously, which again, may in some embodiments be biased towards the unconstrained position, for example by means of a spring or other biasing member 219 as shown in FIGS. 4-6. The fixed elements 224 comprise a ramp with tapers outwardly towards the distal direction.

FIGS. 14 and 15 show the medicament delivery system 300 in condition before use of the medicament delivery device 100. In the case of a hold assistance device 200 which is detachable from the medicament delivery device 100, it can be seen that the hold assistance device 200 has been attached to the medicament delivery device 100 by the first and second housing portions 201a, 201b being hinged around the main body 102 and secured in place by means of the locking mechanism 211 described above. In this pre-use condition, the fixed elements 224 are in the disengaged position and the plates 216 are in the unconstrained position.

When the medicament delivery system 300 is to be used, the user removes the cap 110 to expose needle cover 118 in the extended position shown in FIGS. 3 and 14, places the needle cover 118 on the intended injection site and presses the medicament delivery system 300 in the distal direction as described previously. The needle cover 118 presses against the injection site, is moved in the proximal direction against the force of the needle cover biasing member 120 and continues to be moved in the proximal direction until the needle cover 118 reaches the retracted position shown in FIG. 15. At this position, the protrusions 225 of the fixed elements 224 are radially aligned with the apertures 132 in the needle cover 118. The fixed elements 224 are then able to be moved a radially inward direction 215 to be received within the apertures 132, as shown in FIG. 15. This may be by the user pressing on the finger flanges 217 which moves the plates 216 in the distal direction, and the plates 216 then contacting the ramp portion 226 of the fixed elements 224 and urging the fixed elements 224 radially inwardly.

In the exemplary embodiment shown in FIGS. 14-16, each arm 220 is provided with a biasing member, which, in the embodiment shown, may comprise a compression spring 218 acting on the arm 220. Thus, in some embodiments, the fixed elements 224 may move radially inwardly under the action of the biasing member/spring 218 once the fixed elements 224 are radially aligned with the apertures 132 in the needle cover 118. However, it will be appreciated that the arm biasing members 218 may be omitted in some embodiments and the fixed elements 224 and arms 220 may be moved inwardly by the constraining elements/plates 216 moving in the distal direction without the action of additional biasing members 218.

The plates 216 continue to move in the distal direction until they reach the constraining position shown in FIG. 16. In this position, the protrusions 225 of the fixed elements 224 are retained in the apertures 132 in the needle cover 118 and are prevented from moving radially outwardly by the plates 216 with the resulting needle cover 118 movement prevention and hold force reduction as described previously. Furthermore, after delivery of the medicament, in order to allow the needle cover 118 to move back to its extended position, the plates 216 may be moved out of the constraining position, reversing the steps taken previously. Again, this may be done manually by the user or in other embodiments, the plates 216 may be biased towards the unconstrained position, for example by means of a spring or other biasing member 219 as described above. In embodiments comprising biasing members 218, it is envisaged that the biasing force 130 on the needle cover 118 is sufficient to overcome the biasing force of the biasing members 218. The fixed elements 224 can thereby move in a radially outward direction 215 to the position shown in FIG. 15 so that the needle cover 118 is substantially freely moveable between the protrusions 225 of the fixed elements 224 and can return to the position shown in FIG. 14, thus safely and hygienically covering the needle 116.

As with the previously-described embodiment, the arms 220 are provided with biasing members 218 which act to bias the fixed elements 224 and the arms 220 in a radially inward direction with the functional benefit described above. However, in alternative embodiments envisaged within the scope of the present disclosure, there may be provided biasing members 218 which act to bias the fixed elements 224 and arms 220 in a radially outward direction, again with the alternative functional advantages described above. Yet further, it is envisaged within the scope of the present disclosure that the hold assistance device 200 may be provided without fixed element 224/arm 220 biasing members 218, with the same functional and constructional advantages of such configuration as described above.

It is envisaged within the scope of the present disclosure that the fixed elements 224 of the embodiment shown in FIGS. 14-16 could replace the rollers 212 of any of the other embodiments. In such alternative embodiments, the fixed elements 224 and the protrusions 224 thereof would function as described with reference to the rollers 212 described above.

The protrusions 225 and/or fixed elements 224 may comprise any suitable shape within the scope of the present disclosure, for example a cylinder, bar, rod, part-spherical, or any other appropriate shape of protrusion/fixed element.

Figure 17:
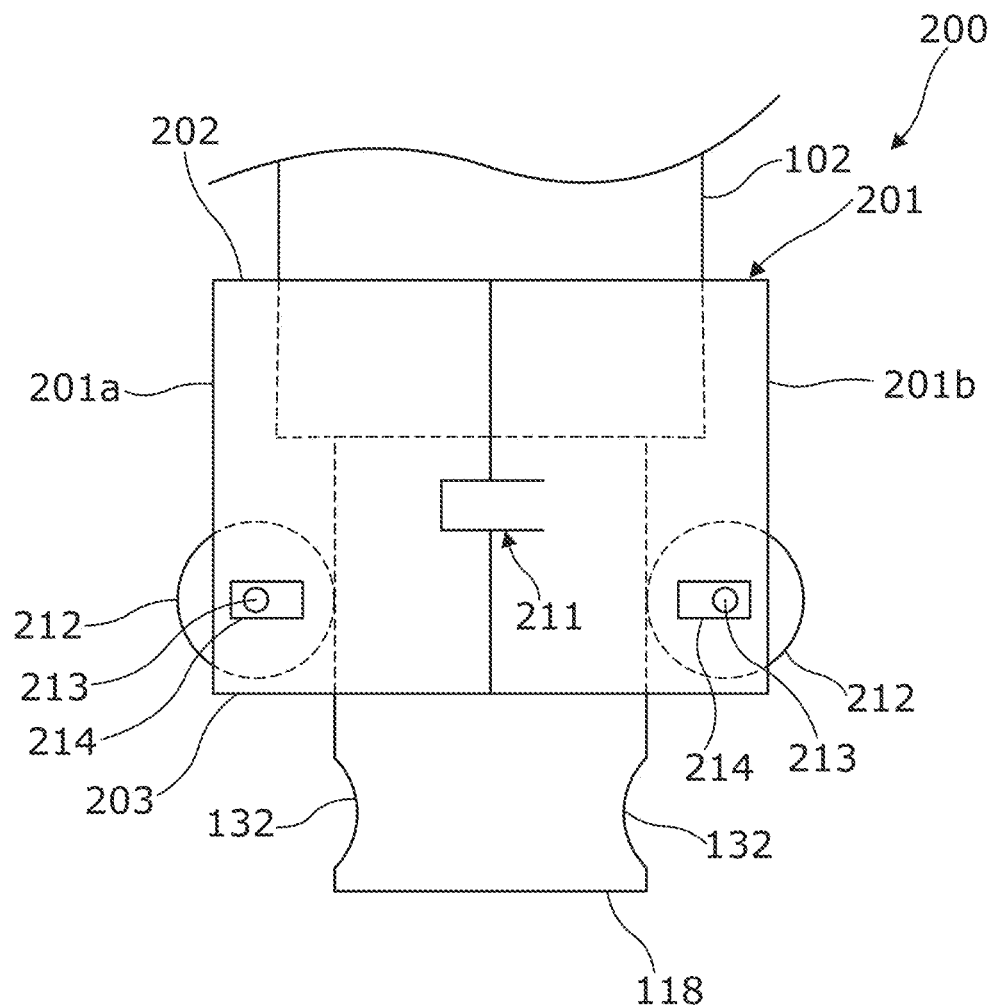
FIG. 17 shows a schematic enlarged side view of a portion of a medicament delivery system similar to that of FIG. 3 but with a hold assistance device of another embodiment of the present disclosure in a first configuration, with the needle cover in an extended position and holding elements in a disengaged position.
Figure 18:
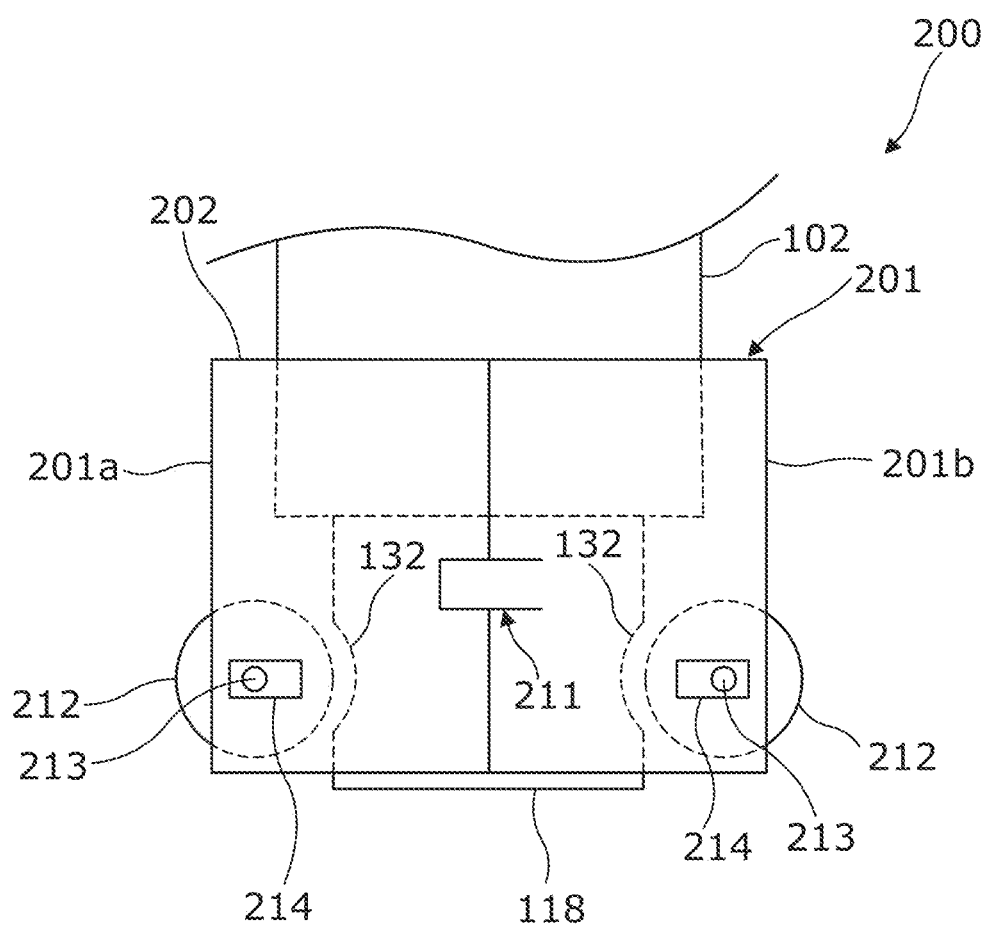
FIG. 18 shows a schematic enlarged side view of a portion of the medicament delivery system of FIG. 17 in a second configuration, with the needle cover in a retracted position and holding elements in a disengaged position.
Figure 19:
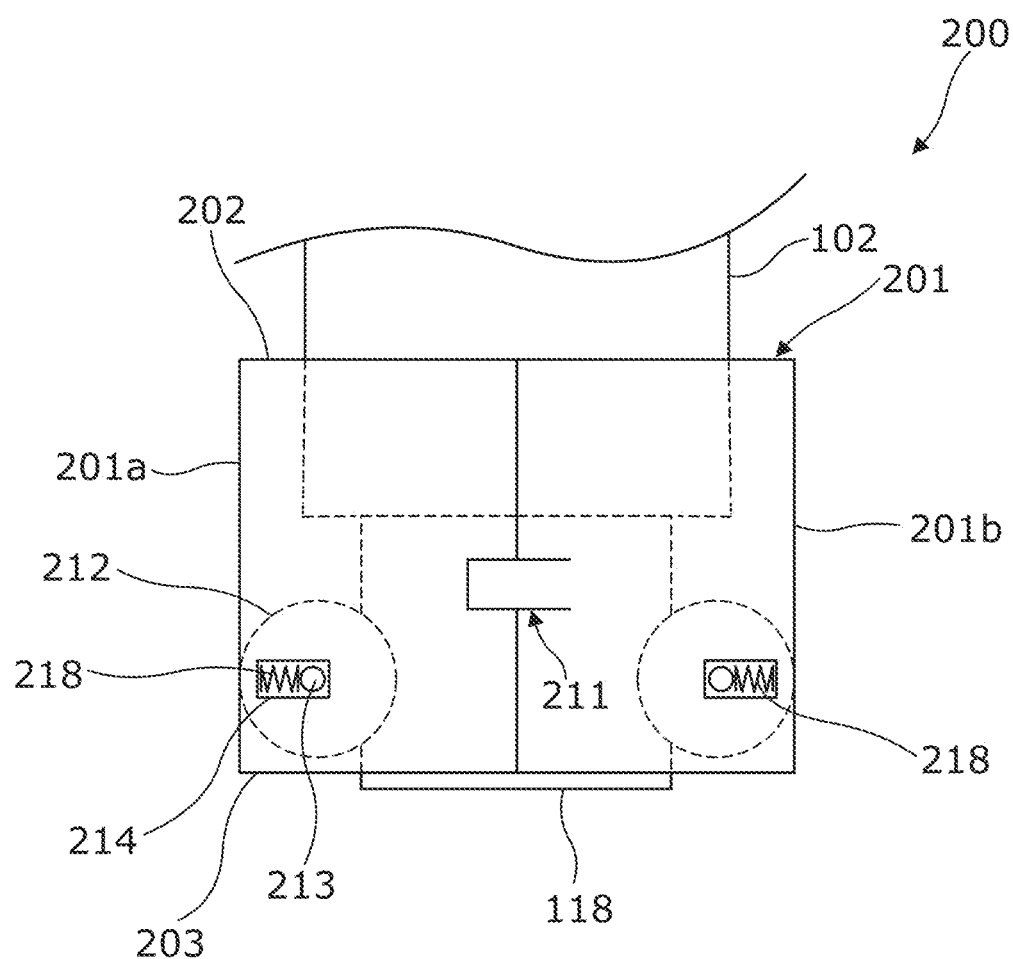
FIG. 19 shows a schematic enlarged side view of a portion of the medicament delivery system of FIGS. 17 and 18 in a third configuration, with the needle cover in a retracted position and holding elements in an engaged position.

FIGS. 17-19 show schematic enlarged side views of a portion of a medicament delivery system 300 similar to that of FIG. 3 and FIGS. 4-6, but comprising a medicament delivery device 100 and a hold assistance device 200 of another embodiment of the present disclosure. Like features in common with the previously-described embodiment of hold assistance device 200 retain the same reference numerals and will not be described in detail again.

A difference with the embodiment shown in FIGS. 17-19 over that shown in FIGS. 4-6 is that the hold assistance device 200 does not comprise the constraining elements or plates 216. The rollers 212 are as previously described, with roller biasing members or springs 218 as described previously. These roller biasing members 218 are configured to bias the rollers 212 in a radially inward direction.

FIG. 17 shows the medicament delivery system 300 in condition before use of the medicament delivery device 100. In the case of a hold assistance device 200 which is detachable from the medicament delivery device 100, it can be seen that the hold assistance device 200 has been attached to the medicament delivery device 100 by the first and second housing portions 201a, 201b being hinged around the main body 102 and secured in place by means of the locking mechanism 211 described above. In this pre-use condition, the rollers 212 are in the disengaged position.

When the medicament delivery system 300 is to be used, the user removes the cap 110 to expose needle cover 118 in the extended position shown in FIGS. 3 and 17, places the needle cover 118 on the intended injection site and presses the medicament delivery system 300 in the distal direction as described previously. The needle cover 118 presses against the injection site, is moved in the proximal direction against the force of the needle cover biasing member 120 and continues to be moved in the proximal direction until the needle cover 118 reaches the retracted position shown in FIG. 18. At this position, the roller 212 are radially aligned with the apertures 132 in the needle cover 118. The rollers 212 are then able to be moved a radially inward direction 215 under the action of the roller biasing members 218 which, in the exemplary embodiment shown in FIGS. 17-19, may comprise a compression spring 218, to be received within the apertures 132, as shown in FIG. 19.

The rollers 212 are held in the apertures 132 in the needle cover 118 by the roller biasing members 218. It will be appreciated that without the constraining elements/plates 216, the rollers are not fully prevented from moving radially outwardly. The rollers 212 may be pushed out of the apertures 132 by the biasing force 130 of the needle cover biasing member 120 when the user releases the hold force on the medicament delivery device 100 and moves the medicament delivery device 100 away from the injection site and the needle cover 118 begins to move back towards the extended position. That is, the biasing force 130 on the needle cover 118 is sufficient to overcome the biasing force of the roller biasing members 218. However, the roller biasing members 218 still serve to lessen the hold force required to hold the medicament delivery device 100 against the patient's skin. Once the rollers 212 have moved in a radially outward direction 215 to the position shown in FIG. 18, the needle cover 118 is substantially freely moveable between the rollers 212 and can return to the position shown in FIG. 17, thus safely and hygienically covering the needle 116.

Figure 20:
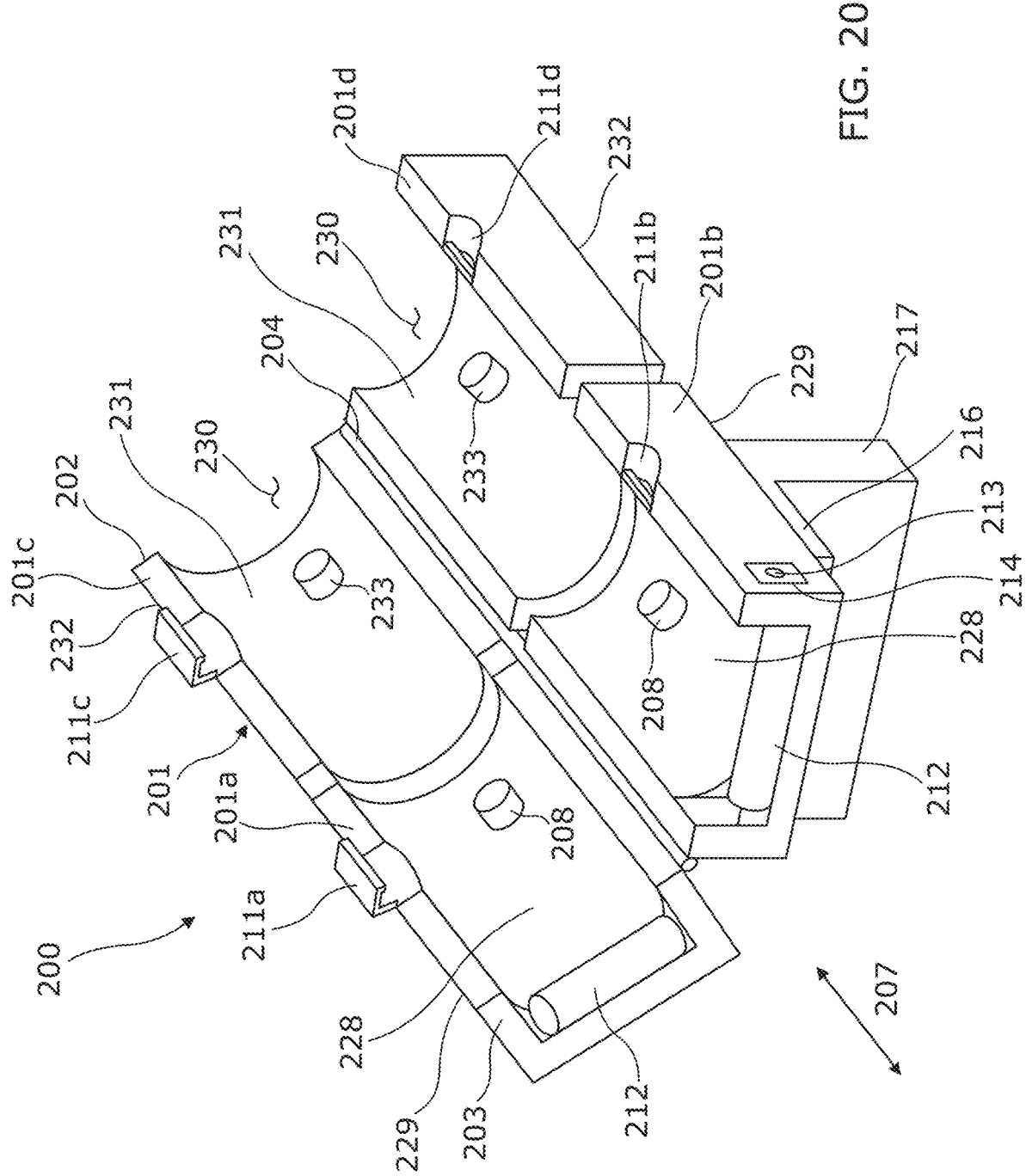
FIG. 20 shows a perspective view of a hold assistance device of another embodiment of the present disclosure, in an opened configuration separate and detached from a medicament delivery device.

FIG. 20 shows a perspective view of a hold assistance device 200 of another embodiment of the present disclosure, shown in an opened configuration separate and detached from a medicament delivery device. The hold assistance device 200 is similar to that shown in FIGS. 3-7, in which like features retain the same reference numerals and will not be described in detail again. As with the previous embodiments, the housing 201 comprises first and second housing portions 201a, 201b which are hingedly connected by a housing hinge 204 in a clam-shell type arrangement.

A difference with the embodiment of FIG. 20 is that the housing 201 further comprises third and fourth housing portions 201c, 201d which are also hingedly connected by the hinge 204 in a clam-shell type arrangement. These third and fourth housing portions 201c, 201d are generally coaxial with the first and second housing portions 201a, 201b and are also moveable between an open position as shown in FIG. 20, where the third and fourth housing portions 201c, 201d are hinged apart, to a closed configuration (not shown). In the closed configuration, the third and fourth housing portions 201c, 201d can clamp around the main body 102 of the medicament delivery device 100. As with the earlier embodiments, the housing 201 is configured to remain fixed, i.e. stationary, relative to the main body 102—i.e. the housing 201 is not movable relative to the main body 102 when the hold assistance device 200 is coupled to the medicament delivery device 100. The connection between the housing 201 and the main body 102 may though be configured to be removable, such that the hold assistance device 200 may be removed from the medicament delivery device 100.

The housing 201 comprises a proximal end 202 and a distal end 203, which define an axial direction 207 and a generally cylindrical passage 230 when in the closed configuration which is arranged to receive and circumscribe the main body 102 of the medicament delivery device 100. However, in other embodiments, the passage 230 can be configured to any other suitable shape to accommodate the main body 102 of the medicament delivery device 100 to which it is intended to be coupled. The third and fourth housing portions 201c, 201d comprise an inner surface 231 and an outer surface 232. The inner surface 231 defines an inner surface of the passage 230 and is configured to be fixedly coupled to the medicament delivery device 100 and to interface therewith.

The third and fourth housing portions 201c, 201d comprise alignment features 233 which are engageable with cooperating alignment features 209 on the medicament delivery device 100 similarly to the function of the alignment features 208 on the first and second housing portions 201a, 201b of the earlier embodiments. In the exemplary embodiment shown in FIG. 20, the first and second housing portions 201a, 201b also comprise the alignment features 208, although these may be omitted given the alignment features 233 on the third and fourth housing portions 201c, 201d. The alignment features 233 comprise a protrusion projecting inwardly from the inner surface 231 of each housing portion 201c, 201d. In the medicament delivery device 100 with which the hold assistance device 200 is configured to be used, the alignment features 209 comprise recesses or apertures in the main body 102 (see FIG. 2). These alignment features 233 on the hold assistance device 200 are configured to be received in the recesses or apertures 209 in the main body 102 and thereby locate the hold assistance device 200 in the correct position for it to be fixedly coupled to the medicament delivery device 100 and to function as intended. However, it will be appreciated that alternative forms of alignment features are intended within the scope of the present disclosure, for example, other shaped projections and corresponding recesses one or other of the hold assistance device 200 and medicament delivery device 100, or a projection or lip on the hold assistance device that may locate over a distal end of the main body 102 of the medicament delivery device 100. Furthermore, in some medicament delivery devices 100, a dosing window 210 is provided on the main body 102 to enable the dose of medicament to be viewed during the medicament delivery process, which may additionally assist the user to determine when the complete dose of medicament has been delivered. In some embodiments, the alignment feature(s) 233 on the hold assistance device 200 may be configured to engage with the or each dosing window 210 to correctly locate the hold assistance device 200 on the medicament delivery device 100.

The hold assistance device 200 comprises a locking mechanism 211 to secure the third and fourth housing portions 201c, 201d in the closed position. In the exemplary embodiment shown, the locking mechanism 211 comprises a locking catch or arm 211c formed on the third housing portion 201c. The locking mechanism 211 also comprises a corresponding locking recess or notch 211d formed on the fourth housing portion 201d. The locking mechanism 211 is operable such that when the housing 201 is fitted around the main body 102 and the third and fourth housing portions 201c, 201d are moved into the closed position, the locking catch 211c engages with the locking recess 211d and retains the third and fourth housing portions 201c, 201d in the closed position.

The hold assistance device 200 of FIG. 20 is configured to be connected to a medicament delivery device in two stages. Firstly, the third and fourth housing portions 201c, 201d are clamped around the main body 102 to securely attach the hold assistance device 200 to the medicament delivery device 100. At this initial stage, the first and second housing portions 201a, 201b remain in the open condition. In some embodiments of medicament delivery device 100, the cap 110 may be sized such that the first and second housing portions 201a, 201b are unable to fully close until the cap has been removed. For example, some caps 110 may be large to enable users with limited dexterity to more easily remove the cap 110 to use the device. When the medicament delivery system 300 is to be used, the user removes the cap 110 to expose the needle cover 118 in the extended position. The user then closes the first and second housing portions 201a, 201b around the medicament delivery device and uses the locking mechanism to secure the first and second housing portions 201a, 201b in the closed position. At this point, the rollers 212 are in the disengaged position and the plates 216 are in the unconstrained position. Thereafter, operation of the medicament delivery system is the same as described previously with reference to the embodiment shown in FIGS. 3-7.

It is intended within the scope of the present disclosure that the embodiments of hold assistance device with only first and second housing portions 201a, 201b may be coupled to a medicament delivery device 100 before the cap 110 is removed, or may be coupled to a medicament delivery device 100 after cap removal, depending on the configuration of medicament delivery device and cap.

It is intended within the scope of the present disclosure that the configuration of hold assistance device having first and second housing portions 201a, 201b, and also the third and fourth housing portions 201c, 201d, could be applied to any embodiment of hold assistance device described previously, for example comprising pivoting arms, flexible arms, fixed elements in place of the rollers, or embodiments without the constraining elements.

Although the constraining elements are shown and described as being plates 216, it is intended within the scope of the present disclosure that alternative configurations of constraining elements may be provided, for example, arcuate part-circular shells, a part of fully circular ring, collar or other axially moveable member. In particular, in embodiments in which the hold assistance device 200 is formed integrally with the medicament delivery device 100, the constraining element may be a single ring, collar or other axially moveable member. Furthermore, in such embodiments intended within the scope of the present disclosure where the hold assistance device 200 is formed integrally with the medicament delivery device 100, the housing 201 or at least part of the housing 201 may be formed integrally with the main body 102 of the medicament delivery device 100. Such embodiments could comprise features of any of the previously-described embodiments, although the housing 201 would not be detachable from the main body 102, and may not comprise the hinge 204 and locking mechanism 211.

Figure 21:
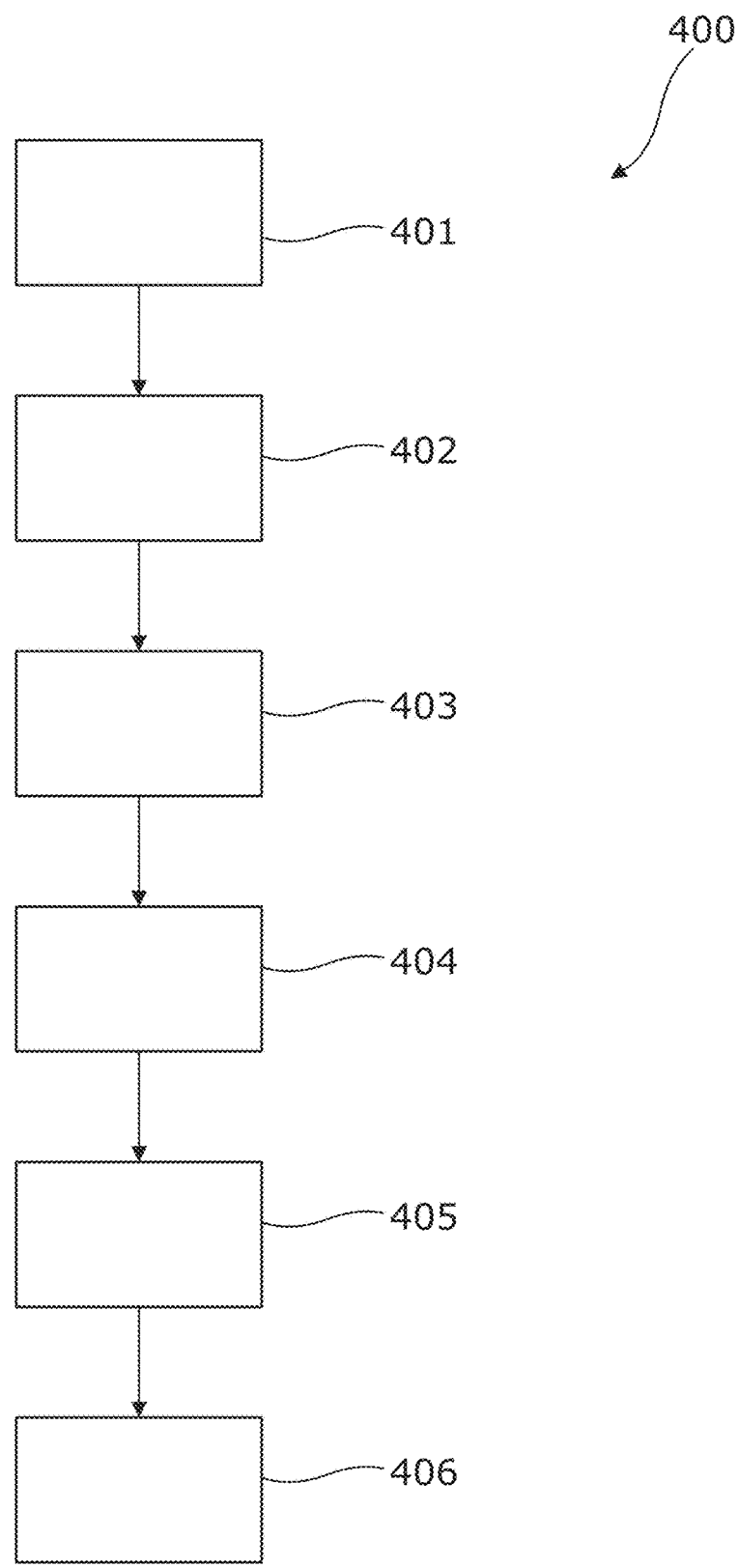
FIG. 21 shows a flowchart illustrating the steps of a method of operating a medicament delivery system.

FIG. 21 shows a flowchart depicting an exemplary method 400 of operating a medicament delivery system 300, for example medicament delivery systems 300 as described above. The exemplary method 400 of FIG. 21 comprises a step 401 of coupling the housing 201 to the main body 102, in order to couple the hold assistance device 200 to the medicament delivery device 100. In step 402, the needle cover 118 is moved from the extended position to the retracted position, such that, for example, the needle cover 118 is retracted inside the main body 102 such that the needle 116 is exposed, to place the medicament delivery device 100 in a state ready for medicament to be delivered from the needle 116 to an injection site of a patient.

In step 402, the needle cover 118 may be moved from the extended position to the retracted position for example by placing the medicament delivery device 100 against the skin of a patient at an injection site, and applying a force in the distal direction in a direction towards the injection site, thus pushing the needle cover 118 against the skin and causing it to be pushed inside the main body 102 to retract thereinside.

An optional step 403 of the method may comprise a user moving the constraining elements, for example plates 216, from the unconstrained position to the constrained position. This may be by pressing on the finger flanges 217 in the distal direction.

Step 404 of the method 400 comprises moving holding elements (for example, rollers 212 or fixed elements 224) from the disengaged position to the engaged position. Step 403 may occur by the holding elements being automatically moved into the engaged position by means of a biasing force on the holding elements, once the apertures 132 in the needle cover 118 are aligned with the holding elements. Alternatively, step 404 may occur concurrently or at least partially concurrently with optional step 403 such that movement of the constraining elements causes the holding elements to be moved from the disengaged position to the engaged position.

An optional step 405 of the method may comprise a user moving the constraining elements, for example plates 216, from the constrained position to the unconstrained position. This may be by releasing pressure on the finger flanges 217 in the distal direction, or actively moving the finger flanges 217 in the proximal direction.

Step 406 of the method comprises releasing the holding action of the needle cover 118 by moving the holding elements from the engaged position to the disengaged position. Step 406 may occur by the holding elements being automatically moved into the disengaged position by means of a biasing force on the holding elements, once the apertures 132 in the needle cover 118 are aligned with the holding elements. Alternatively, step 406 may occur under the action of the needle cover biasing member 120 biasing force 130 urging the needle cover 118 towards the extended position and pushing the holding elements out of the apertures 132. Step 406 may occur concurrently or at least partially concurrently with optional step 405 such that movement of the constraining elements to the unconstrained position causes or allows the holding elements to be moved from the engaged position to the disengaged position.

In the method 400, between step 403/404 of moving the holding elements into the engaged position/optionally moving the constraining elements into the constrained position, and step 405/406 of releasing the holding action of the holding elements/moving the constraining elements towards the unconstrained position, a user of the medicament delivery system 300 may hold the medicament delivery device 100 for a required duration of time at an injection site of a patient. For example, the user may hold the medicament delivery device 100 at the injection site for the amount of time required for completion of delivery of a medicament from the needle 116 to be complete.

The method 400 may further comprise a step (not shown) of moving the needle cover 118 from the retracted position back into the extended position, such that the needle 116 is covered, which may be desirable for reasons of safety and hygiene. The needle cover 118 may be moved from the retracted position back into the extended position by, for example, removing a user hold force acting on the medicament delivery device 100, for example by moving the medicament delivery device 100 away from an injection site of a patient. For example, by moving the medicament delivery device 100 in the proximal direction away from the skin of a patient, this may remove the user hold force pushing the needle cover 118 inside the housing 102 as a result of pressing the needle cover 118 against the skin, such that when the medicament delivery device 100 is moved away, the needle cover 118 is permitted to extend outwards again under the action of the biasing force 130 of the needle cover biasing member 120.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device/medicament delivery device
102—outer casing/housing/main body
104—reservoir
106—plunger
108—collar
110—cap
112—longitudinal axis
113—stopper
114—rear casing
116—needle
118—needle shroud/sleeve/cover
120—control spring/needle cover biasing member
122—drive spring
126—distal end
128—proximal end
130—biasing force
132—apertures/cut-outs in needle shroud/sleeve/cover
134—recesses in outer casing/housing/main body
200—hold assistance device
201—housing
201a—first housing portion
201b—second housing portion
201c—third housing portion
201d—fourth housing portion
202—proximal end of housing
203—distal end of housing
204—hinge member
207—axial direction
208—alignment features on hold assistance device
209—alignment features on medicament delivery device
210—dosing window on main body of medicament delivery device
211—locking mechanism of hold assistance device
211a—locking catch/arm
211b—locking recess/notch
212—rollers—holding elements
213—spindle elements of rollers
214—slots to receive spindle elements 215—roller radial movement direction
216—plates—constraining elements
217—finger flange of constraining elements
218—holding element biasing member
219—constraining element biasing member
220—pivotable arms
221—pivot of pivotable arms
222—flexible arms
223—fixed point of flexible arms
224—fixed elements—holding elements
225—protrusions of fixed elements
226—ramp portion of fixed elements
228—inner surface of first/second housing portions
229—outer surface of first/second housing portions
230—passage in housing
231—inner surface of third/fourth housing portions
232—outer surface of third/fourth housing portions
233—alignment features on hold assistance device
400—method
401—method step
402—method step
403—method step
404—method step
405—method step
406—method step

The invention claimed is:

1. A hold assistance device for use with a medicament delivery device which comprises a moveable needle cover, the hold assistance device comprising:
a housing configured to be coupled to the medicament delivery device, the housing comprising a proximal end and a distal end that define an axis between the proximal end and the distal end; and
a holding element coupled to the housing and moveable relative to the housing in a direction substantially normal to the axis of the housing between a disengaged position and an engaged position,
wherein the holding element is disposed outwardly from the axis in the disengaged position, is disposed inwardly towards the axis in the engaged position and is configured in the engaged position such that the holding element can engage with an aperture or a recess in a needle cover of a medicament delivery device when the hold assistance device is coupled thereto, to resist movement of the needle cover relative to the housing, and wherein the holding element comprises a roller.

2. The hold assistance device according to claim 1, wherein the housing comprises a passage extending between the proximal end and the distal end to receive a medicament delivery device with which the hold assistance device is to be used, the passage defining the axis.

3. The hold assistance device according to claim 1, wherein the roller comprises one or more spindle elements in slots at opposite ends of the roller to enable the roller to move relative to the housing in a direction substantially normal to the axis of the housing between the disengaged position and the engaged position.

4. The hold assistance device according to claim 1, comprising a holding element biasing member configured to bias the holding element inwardly relative to the axis of the housing towards the engaged position.

5. The hold assistance device according to claim 1, wherein the holding element is mounted to one or more arms, wherein each of the one or more arms is moveable to allow the hold element to move between the disengaged position and the engaged position.

6. The hold assistance device according to claim 5, wherein each of the one or more arms is pivotable about a pivot point.

7. The hold assistance device according to claim 5, wherein each of the one or more arms is resiliently deformable.

8. The hold assistance device according to claim 1, further comprising a constraining element coupled to the housing and moveable between an unconstrained position in which the constraining element enables the holding element to remain in the disengaged position, and a constrained position in which the constraining element retains the holding element in the engaged position.

9. The hold assistance device according to claim 8, wherein the constraining element is moveable in an axial direction of the housing between the unconstrained position and the constrained position.

10. The hold assistance device according to claim 8, wherein holding element and the constraining element are configured such that as the constraining element is moved from the unconstrained position towards the constrained position, the constraining element contacts the holding element and urges the holding element from the disengaged position to the engaged position.

11. The hold assistance device according to claim 8, wherein the constraining element comprises a plate slidably mounted to the housing.

12. The hold assistance device according to claim 8, comprising a constraining element biasing member configured to bias the constraining element into the unconstrained position.

13. The hold assistance device according to claim 8, wherein the constraining element comprises a finger flange protruding outwardly with respect to the axis of the housing to facilitate a user moving the constraining element from the unconstrained position to the constrained position.

14. The hold assistance device according to claim 1, wherein the housing comprises first and second housing portions which are moveable from an open position to allow placement of a medicament delivery device within the housing, and a closed position in which the housing is fixedly secured to the medicament delivery device within the housing.

15. The hold assistance device according to claim 14, wherein the first and second housing portions are hingedly connected by a hinge member and are pivotable relative to each other to move between the open position and the closed position.

16. The hold assistance device according to claim 14, wherein the housing comprises a locking mechanism configured to secure the first and second housing portions in the closed position.

17. The hold assistance device according to claim 14, wherein the housing further comprises third and fourth housing portions which are moveable from an open position to allow placement of a medicament delivery device within the housing, and a closed position in which the housing is fixedly secured to the medicament delivery device within the housing, such that the hold assistance device may be fixedly secured to a medicament delivery device by placing the third and fourth housing positions in the closed position around the medicament delivery device, before the first and second housing portions are moved from the open position to the closed position.

18. The hold assistance device according to claim 17, wherein the third and fourth housing portions are hingedly connected and are pivotable relative to each other to move between the open position and the closed position.

19. The hold assistance device according to claim 18, wherein the housing comprises a locking mechanism configured to secure the third and fourth housing portions in the closed position.

20. The hold assistance device according to claim 18, when dependent on claim 16, wherein the first and second housing portions are hingedly connected by a same hinge member which hingedly connects the third and fourth housing portions.

21. The hold assistance device according to claim 14, wherein the housing comprises at least one alignment feature configured to engage with a corresponding alignment feature of the medicament delivery device to which the hold assistance device is to be attached, to ensure the housing is correctly located on the medicament device when in use.

22. A medicament delivery system comprising a hold assistance device and a medicament delivery device,
wherein the hold assistance device comprises:
a housing configured to be coupled to the medicament delivery device, the housing comprising a proximal end and a distal end that define an axis between the proximal end and the distal end; and
a holding element coupled to the housing and moveable relative to the housing along an axis of the housing between a disengaged position and an engaged position,
wherein the holding element is disposed outwardly from the axis in the disengaged position and is disposed inwardly towards the axis in the engaged position and is configured in the engaged position such that the holding element can engage with an aperture or a recess in a needle cover of a medicament delivery device when the hold assistance device is coupled thereto, to resist movement of the needle cover relative to the housing, and
wherein the medicament delivery device comprises:
a main body configured to receive a medicament cartridge and comprising a proximal end and a distal end;
a needle for delivery of medicament from the medicament cartridge disposed towards the distal end of the main body;
a needle cover axially movable relative to the main body between (i) an extended position in which the needle cover extends from the distal end of the main body and covers a distal end of the needle which protrudes from the main body and (ii) a retracted position in which the needle cover is arranged in a proximal position relative to the extended position such that the distal end of the needle protrudes from a distal end of the needle cover, wherein the needle cover comprises at least one aperture or recess towards the distal end of the needle cover; and
a needle cover biasing member configured to bias the needle cover axially in a distal direction towards the extended position,
wherein the housing of the hold assistance device is configured to be coupled to the main body, and when the housing is coupled to the main body, the holding element, in the engaged position, is configured to engage with the aperture or recess in the needle cover in the retracted position to resist movement of the needle cover axially in the distal direction towards the extended position.

23. The medicament delivery system according to claim 22, wherein the hold assistance device is a separate device to the medicament delivery device and is attached to the medicament delivery device.

24. The medicament delivery system of claim 22, wherein the medicament delivery system further comprises a medicament cartridge containing medicament.

25. A method of operating a medicament delivery system comprising a hold assistance device and a medicament delivery device,
wherein the hold assistance device comprises:
a housing configured to be coupled to the medicament delivery device, the housing comprising a proximal end and a distal end that define an axis between the proximal end and the distal end; and
a holding element coupled to the housing and moveable relative to the housing along an axis of the housing between a disengaged position and an engaged position,
wherein the holding element is disposed outwardly from the axis in the disengaged position and is disposed inwardly towards the axis in the engaged position and is configured in the engaged position such that the holding element can engage with an aperture or a recess in a needle cover of a medicament delivery device when the hold assistance device is coupled thereto, to resist movement of the needle cover relative to the housing, and
wherein the medicament delivery device comprises:
a main body configured to receive a medicament cartridge and comprising a proximal end and a distal end;
a needle for delivery of medicament from the medicament cartridge disposed towards the distal end of the main body;
a needle cover axially movable relative to the main body between: an extended position in which the needle cover extends from the distal end of the main body and covers a distal end of the needle which protrudes from the main body; and a retracted position in which the needle cover is arranged in a proximal position relative to the extended position such that the distal end of the needle protrudes from a distal end of the needle cover, wherein the needle cover comprises at least one aperture or recess towards the distal end of the needle cover; and
a needle cover biasing member configured to bias the needle cover axially in a distal direction towards the extended position,
wherein the housing of the hold assistance device is configured to be coupled to the main body, and when the housing is coupled to the main body, the holding element, in the engaged position, is configured to engage with the aperture or recess in the needle cover in the retracted position to resist movement of the needle cover axially in the distal direction towards the extended position, and
wherein the method comprises:
coupling the housing to the main body;
moving the needle cover from the extended position to the retracted position; and
moving the holding element into the engaged position such that the holding element engages with the aperture or recess in the needle cover to resist movement of the needle cover axially in the distal direction towards the extended position.

* * * * *